US007820769B2

(12) United States Patent
Seifalian et al.

(10) Patent No.: US 7,820,769 B2
(45) Date of Patent: Oct. 26, 2010

(54) POLYMER FOR USE IN CONDUITS, MEDICAL DEVICES AND BIOMEDICAL SURFACE MODIFICATION

(75) Inventors: Alexander Seifalian, London (GB); Henryk Salacinski, London (GB); Kaila Srai, London (GB); Bala Ramesh, London (GB); Arnold Darbyshire, London (GB); Steve Hancock, London (GB)

(73) Assignee: UCL Biomedica PLC, London (GB)

( * ) Notice: Subject to any disclaimer, the term of this patent is extended or adjusted under 35 U.S.C. 154(b) by 863 days.

(21) Appl. No.: 10/586,649

(22) PCT Filed: Jan. 20, 2005

(86) PCT No.: PCT/GB2005/000189

§ 371 (c)(1),
(2), (4) Date: Jul. 19, 2006

(87) PCT Pub. No.: WO2005/070988

PCT Pub. Date: Aug. 4, 2005

(65) Prior Publication Data

US 2008/0233164 A1 Sep. 25, 2008

(30) Foreign Application Priority Data

Jan. 20, 2004 (GB) .................................. 0401202.7

(51) Int. Cl.
*C08L 83/10* (2006.01)
(52) U.S. Cl. ........................... 525/474; 528/44; 528/45; 528/67; 528/28
(58) Field of Classification Search ............. 528/44–45, 528/67, 28; 525/474
See application file for complete search history.

(56) References Cited

U.S. PATENT DOCUMENTS

| | | | |
|---|---|---|---|
| 4,617,340 | A | 10/1986 | Tanaka et al. |
| 4,631,329 | A | 12/1986 | Gornowicz et al. |
| 4,739,013 | A * | 4/1988 | Pinchuk ...................... 525/101 |
| 4,839,443 | A | 6/1989 | Akutsu et al. |
| 4,942,212 | A | 7/1990 | Hanada et al. |
| 5,024,893 | A | 6/1991 | Hanada et al. |
| 5,128,408 | A | 7/1992 | Tanaka et al. |
| 5,430,121 | A | 7/1995 | Pudleiner et al. |
| 5,589,563 | A | 12/1996 | Ward et al. |
| 5,863,627 | A | 1/1999 | Szycher et al. |
| 6,313,254 | B1 | 11/2001 | Meijs et al. |
| 2002/0028901 | A1 | 3/2002 | Gunatillake et al. |
| 2003/0018156 | A1 | 1/2003 | Meijs et al. |
| 2003/0097120 | A1 | 5/2003 | Santerre |
| 2004/0116641 | A1 | 6/2004 | Mather et al. |
| 2004/0122174 | A1 | 6/2004 | Mather et al. |
| 2004/0122184 | A1 | 6/2004 | Mather et al. |
| 2005/0010275 | A1 * | 1/2005 | Sahatjian et al. ........... 623/1.11 |

FOREIGN PATENT DOCUMENTS

| | | |
|---|---|---|
| EP | 0 277 816 A | 8/1988 |
| EP | 0 324 946 A1 | 7/1989 |
| EP | 0 416 765 A2 | 3/1991 |
| JP | 04-304224 | 10/1992 |
| JP | 9-194560 | 7/1997 |
| JP | 2006-503170 | 1/2006 |
| WO | 02/098477 A | 12/2002 |
| WO | WO 02/098477 A2 | 12/2002 |
| WO | WO 2004/01152 A1 | 2/2004 |
| WO | 2004/032799 A | 4/2004 |
| WO | WO 2004/032799 A2 | 4/2004 |
| WO | WO 2004/033515 A2 | 4/2004 |

OTHER PUBLICATIONS

Seifalian et al, Tissue Enginnering of Vascular Prosthetic Grafts, 1999 R.G. Landes.

(Continued)

*Primary Examiner*—Kuo-Liang Peng
(74) *Attorney, Agent, or Firm*—Nixon & Vanderhye, P.C.

(57) ABSTRACT

A copolymer comprising (a) one or more pendant group segments and (b) one or more polyol segments, each of said segments being linked to one or more further segments which may be the same or different,
wherein said one or more pendant group segments are the same or different and are selected from:
(i) siloxane segments;
(ii) segments containing phosphoryl choline or a derivative or analogue thereof;
(iii) segments containing a di- or trifluoromethyl group;
(iv) heparin-like segments containing a group of formula (XII)

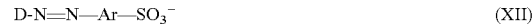

$$D-N=N-Ar-SO_3^-  \quad (XII)$$

wherein D is an aliphatic or aromatic group and $Ar-SO_3^-$ comprises one or more linked aryl and/or heteroaryl groups, at least one of the aryl and/or heteroaryl groups having an $SO_3^-$ substituent; and
(v) segments containing a group of formula (I)

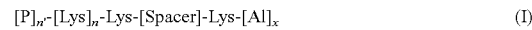

$$[P]_{n'}\text{-}[Lys]_n\text{-}Lys\text{-}[Spacer]\text{-}Lys\text{-}[Al]_x \quad (I)$$

wherein:
[Al] is an inert amino acid;
x is 0, 1, 2 or 3;
[Spacer] is a fatty acid, amino acid, peptide or PEG;
$[P]_{n'}\text{-}[Lys]_n$ is a dendritic structure formed from n lysine groups and terminating in n' groups P;
n is an integer of from 1 to 15;
n' is zero or an integer of up to 16; and
each P is the same or different and is an amino acid or a peptide having up to 25 amino acids,
and wherein at least a part of each of said pendant group segment(s) is on a side chain of the copolymer.

The copolymer is useful in the production of implantable devices such as vascular grafts.

38 Claims, 8 Drawing Sheets

OTHER PUBLICATIONS

Mohri, H et al, Peptides 1995, 16: p. 263.
Woods, A., et al, Mol. Biol. Cell, 1993; 4: p. 605.
Haverstick, DM et al, Blood; 1985; 66: p. 946.
Freer, R. J., et al, 1979; Peptides, structure and biological function; Proceedings of the sixth American peptide symposium; Gross, E and Meinhofter, M., eds.:749.
Proctor, R.A., Rev. Infect. Dis. 1987; 9: p. 317.
Zhang, H. et al, Biomaterials Mar. 2002; 23(6): 1485-94.
J.P. Tam, Proc. Natl. Sci. USA, 1988, 85, 5409.
H. Rink (1978) Tetrahedron Lett., 28, 3787.
Jaffe et al, J. Clin. Invest. 1973; 52; 2745-56.
Zilla et al, J. Vasc. Sug. 1990; 12: pp. 180-189.
Edwards, A. et al, J. Biomat. App. 1995; 10: pp. 171-187.
WPI abstract AN 1988-142716 [25] & JP 63083121 A.
J.P. Tam; Synthetic Peptides; Approaches to Biological Problems, 3-18 (1989).
D.N. Posnett et al, A novel Method for Producing Anti-Peptide Antibodies; J. Biol. Chem. 263, 1719 (1988).
Fu et al, Polymer 42 (2001) 599-611.
Schwab et al, Mat. Res. Soc. Symp. Proc. 519, Apr. 13, 1998 Materials Research Society, 21-27.
Fan et al, Journal of Applied Polymer Science, vol. 24, 2552-2558 (1999).
Molander et al, Tetrahedron 54 (1998) 9289-9302.
Ward, "Thermoplastic Silicone-Urethane Copolymers: A New Class of Biometical Elastomers", Medical Device & Diagnostic Industry Magazine, Apr. 2000 (including Table I).
Barry Arkles, Commercial Applications of Sol-Gel-Derived Hybrid Materials, MRS Bulletin, May 2001, 402-408.
Seifalian et al, J. Biomed. Mater. Res. 2001, 55, 637-44.
Aucoin L. et al, J. Miomater. Sci. Polym. Ed., 2002, 13(4):447-62.
Merrett et al, J. Biomed Res. Dec. 1, 2003; 67A(3):981-93.
Li et al, Biomaterials, Oct. 2001 (19):2595-9.
Childs et al, Biomacromolecules, 2001 Summer; 2(2):526-37.
Database WPI, Section Ch, Week 197950, Derwent Publications Ltd., London, GB; AN 1979-90714B & SU 654634 A (Mar. 30, 1979).
International Search Report for PCT/GB2005/000189 dated Jun. 2, 2005.

* cited by examiner

Silsesquioxane 1

Silsesquioxane 2

Silsesquioxane 3

Silsesquioxane 4

Fig.1e.    Silsesquioxane 5
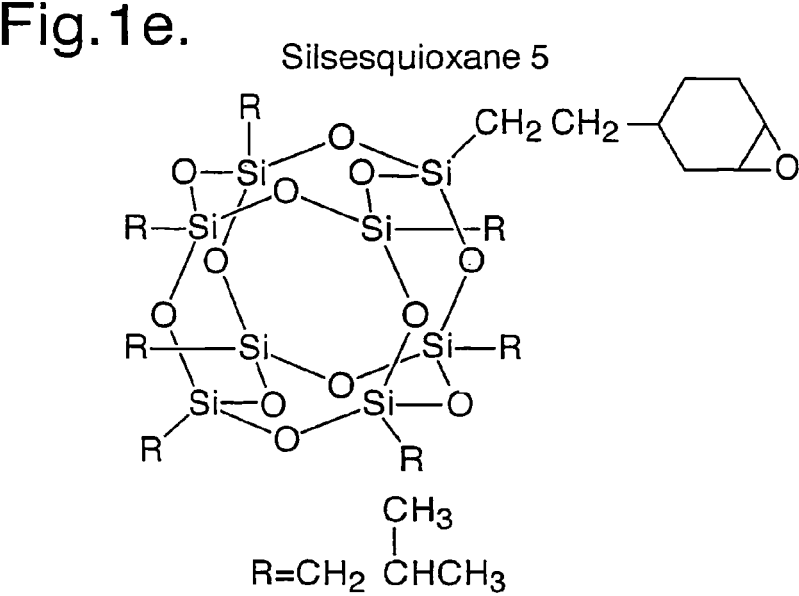
$R = CH_2 \overset{CH_3}{\underset{}{CHCH_3}}$
Fig.1f.    Silsesquioxane 6
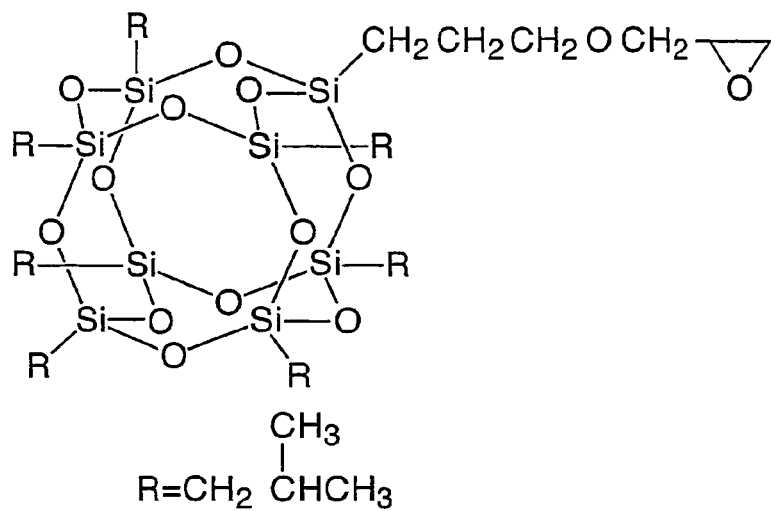
$R = CH_2 \overset{CH_3}{\underset{}{CHCH_3}}$
Fig.2.
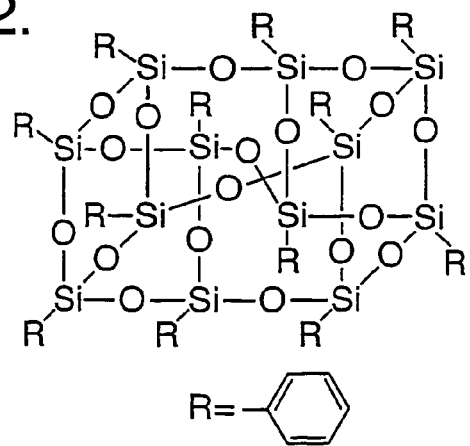

R=CH₂CHCH₃
         |
        CH₃

POLYMER FOR USE IN CONDUITS, MEDICAL DEVICES AND BIOMEDICAL SURFACE MODIFICATION

This application is the US national phase of international application PCT/GB2005/000189 filed 20 Jan. 2005 which designated the U.S. and claims benefit of UK 0401202.7 filed 20 Jan. 2004, the entire contents of each of which are hereby incorporated by reference.

FIELD OF THE INVENTION

The present invention relates to copolymers, typically polyurethane copolymers, having one or more pendant groups attached to the backbone of the polymer, and a process for producing such copolymers. The invention relates, in particular, to siloxane-containing, including silsesquioxane-containing copolymers, typically siloxane-containing and silsesquioxane-containing polyurethane copolymers. The copolymers are useful as implantable devices, in particular in medical applications, including coronary and vascular applications.

BACKGROUND OF THE INVENTION

Atherosclerotic vascular disease in the form of coronary artery and peripheral vascular disease is the largest cause of mortality in both the United States and Europe. Surgical mainstays of therapy for affected vessels include bypass grafting with autologous veins or arteries; however, adequate autologous vein is lacking in many patients. Prosthetic vascular grafts are therefore required.

Several materials are presently available for use as prosthetic vascular grafts and other surgical prostheses. These include polytetrafluoroethylene (PTFE) and Dacron. These two materials are rigid and when used as grafts create a compliance mismatch at the anastomosis. The primary patency rates of PTFE or Dacron grafts is 20 to 30% at 4 to 5 years. A further material which can be used as a vascular graft is polyurethane (PU). This material has the advantage that it is more elastic and therefore more similar to the blood vessel which it is to mimic. PU grafts are thus compliant grafts in the sense that they behave in a similar way to a natural blood vessel in the body. In particular, they flex more readily than PTFE or Dacron grafts when the site at which they are contained flexes.

Compliance is regarded by many as the key attribute required for matching cardiovascular prostheses to the arterial tree. The development of a compliant material is therefore thought to be an important step towards the improvement of clinical performance of small diameter grafts, particularly in low flow situations such as below knee arterial bypass. Obtaining long term compliance has been an elusive goal as currently used grafts rely on an overall external dilation to provide compliance. However, perivascular ingrowth prevents external dilation and thus compliance is lost after a relatively short period of time.

PU based grafts however achieve compliance via a different mechanism. Increases in volume are accommodated by a mechanism of wall compression without the need for external dilation. The use of compliant PU rather than a more rigid material has previously been found to increase the patency rate of the graft (Seifalian et al, Tissue Engineering of Vascular Prosthetic Grafts, 1999 R. G. Landes).

However, the use of any of these materials alone for the graft is problematic: as the blood flows through the graft, particles such as platelets tend to adhere to the surface of the graft or the blood may coagulate, in particular in the area of the anastomoses, in particular the distal anastomosis, but also along the luminal surface of the graft. This causes a narrowing (stenosis) in the inner diameter of the vessel, which is particularly problematic in the context of grafts of low diameter (for example 5 mm or less) where there is little blood flow. The major area which is affected is the distal anastomosis, where the downstream end of the graft-meets the blood vessel. This has mainly been attributed to the lack of coverage by endothelial cells, the natural lining of normal blood vessels. The endothelium has the potential to release anticoagulant and platelet active substances which facilitate normal blood flow.

In order to address this problem, seeding grafts with endothelial cells, both before and during surgery, has been attempted. Broadly, seeding is carried out by extracting endothelial cells from the patient's adipose tissue or a vein and using these cells to coat the inside of the graft, in order to mimic the natural endothelium. Although seeding the graft in this manner has been shown to increase the patency rate, seeded cells adhere very poorly to the graft surface, in particular to PTFE. Indeed, where cells are seeded directly onto the graft lumen, only 1 to 14% of cells remain attached following exposure to blood flow.

Of crucial importance therefore in endothelial seeding is the ability of the seeded cells to resist the shear stress caused by the flow of blood through the vessel. The pulsatile nature of the blood flow makes it particularly likely that the cells will be swept away if not firmly attached to the surface of the graft. Where endothelial seeding is more difficult, e.g. with PTFE, the effect of shear stress is vital, although it is very important when using any graft material.

Numerous techniques have been developed to aid attachment of endothelial cells to the polymer surface. For example, fibronectin glue enriched with RGD (Arg-Gly Asp) has been used to increase adherence of endothelial cells. Various alternative bonding chemistries have also be attempted to attach to the surface of the polymer moieties such as RGD and heparin that aid endothelium formation, as well as other anticoagulants. However, recent in vitro studies have shown that these bonding chemistries lead to alterations in the mechanical properties of the polymer. In vivo studies have also shown that the presence of the anticoagulants on the polymer surface can lead to alterations in the chemical behaviour of the polymer, resulting in aneurismal failure.

For surgical use, the acceptable scope for variation in the physical and chemical properties of the graft is small. The change brought about by bonding anticoagulants and other materials to the surface of the polymer may be sufficient to cause failure of the graft in vivo. A new approach is therefore required, by which biocompatibility of the polymer is improved without the need for such bonding steps.

A further problem associated with PUs is the possibility of degradation in vivo over long periods of time. Clinically, polyurethanes used for permanent implants have a very mixed record due to the variety of degradation mechanisms that come into play, especially in the case of their usage for vascular grafts for lower limb bypass. In such lower limb bypass grafts, the site of degradation has invariably been the amorphous or soft segment, typically an ester, ether or carbonate.

Degradation is a particular problem for materials having heparin attachments. Heparin tends to attract moisture, which in turn attracts biological enzymes. These enzymes cause the polymer to degrade, thus leading to an unacceptably short lifetime for the heparin-bound polymer.

The resistance of hydrolysable polymer structures to hydrolysis can be improved by incorporation of hydrocarbons such as silicones, sulfones, halocarbons and/or isolated carbonyl-containing molecules (ketones) in the polymer structure. Recent work has produced a number of polyurethanes in which siloxane blocks have been incorporated into polyurethanes. However, these structures have been found to have poor mechanical properties, possibly due to the presence of crystalline areas in the polymer. The poor resistance of these types of polymer to tear, and their tendency to discolour, have been noted as particular problems.

Previously known siloxane polymers also have inferior biological properties, noted by their reduced ability to support the growth of endothelial cells used in seeding bypass grafts. An alternative polymer is therefore required which addresses these difficulties by providing improved mechanical properties, as well as improved biological properties, including compatibility to blood and the ability to support endothelial cell growth.

SUMMARY OF THE INVENTION

The present inventors have developed a new polymer, typically a polyurethane polymer and for example a siloxane-containing polymer, which addresses the problems of the prior art and has improved mechanical and biological properties. The present invention therefore provides a copolymer comprising (a) one or more pendant group segments and (b) one or more polyol segments, each of said segments being linked to one or more further segments which may be the same or different, wherein said one or more pendant group segments are the same or different and are selected from:
(i) siloxane segments;
(ii) segments containing phosphoryl choline or a derivative or analogue thereof;
(iii) segments containing a di- or trifluoromethyl group;
(iv) heparin-like segments containing a group of formula (XII)

$$D\text{-}N\!=\!N\text{—}Ar\text{—}SO_3^- \qquad (XII)$$

wherein D is an aliphatic or aromatic group and $Ar\text{—}SO_3^-$ comprises one or more linked aryl and/or heteroaryl groups, at least one of the aryl and/or heteroaryl groups having an $SO_3^-$ substituent; and
(v) segments containing a group of formula (I)

$$[P]_{n'}\text{-}[Lys]_n\text{-}Lys\text{-}[Spacer]\text{-}Lys\text{-}[A1]_x \qquad (I)$$

wherein:
  [A1] is an inert amino acid;
  x is 0,1,2 or 3;
  [Spacer] is a fatty acid, amino acid, peptide or PEG;
  $[P]_{n'}\text{-}[Lys]_n$ is a dendritic structure formed from n lysine groups and terminating in n' groups P;
  n is an integer of from 1 to 15;
  n' is zero or an integer of up to 16; and
  each P is the same or different and is heparin, an amino acid or a peptide, and wherein at least a part of each of said pendant group segment(s) is on a side chain of the copolymer. The copolymers are typically polyurethanes, and each of the segments is therefore typically linked to neighbouring segments via urea or urethane linkages.

The copolymers of the invention contain one or more functional groups attached in a pendant manner (i.e. on a side chain) to the copolymer backbone. The specific pendant groups to be included in the polymer can be chosen so as to tailor the properties of the resulting copolymer to the application for which the copolymer is to be used. Thus, for example, pendant siloxane groups can be included when improved strength and biostability are required; pendant phosphoryl choline-derived groups can be included to improve blood compatibility, pendant di- or trifluoromethyl-containing groups can be included to decrease thrombogenicity and possibly also to interfere with the appearance of platelets in blood which contacts the polymer; and pendant heparin-like groups can be included to provide improved blood compatibility without attracting moisture to the polymer.

Additionally, the invention provides a technique by which a variety of different peptides can be attached to a pendant arm of the polymer. Thus, the invention enables the skilled person to introduce compatabilising peptides such as heparin and RGD, or growth factor peptides such as those derived from VEGF (vascular endothelial growth factor) or IGF (insulin-like growth factor, of which there are several sources, e.g. IGF-1 and IGF-2). Thus, by incorporating one or more of these different pendant groups, the skilled person is able to specifically design the properties of the resulting copolymer.

The incorporation of compatabilising peptides into the polymer has the advantage that the surface of the polymer may be pre-coated with compatabilising peptide prior to insertion of the graft into a patient. This leads to immediate results in terms of providing blood compatibility. In contrast, previous methods which relied upon seeding the surface of the polymer, and a gradual build up of endothelial coating in vivo, have a relatively poor blood compatibility immediately after insertion of the graft.

In a particular embodiment, heparin-like groups, particularly heparin-like cages, are incorporated into the polymer. These materials import to the graft material similar biocompatibility properties as are achieved by heparin itself. However, such polymers, in particular those containing cage-like heparin groups, do not adsorb moisture to the same extent as heparin and the lifetime of the material is thus improved. Polymers containing cage-like heparin groups also provide enhanced strength properties.

In a further embodiment, one or more pendant groups on the polymer contains a $\text{—}CF_3$ or $\text{—}CF_2\text{—}$ group. Such pendant groups mirror the properties of PTFE and therefore have good mechanical properties including high strength, as well as the ability to reduce protein adsorption. Such polymers are therefore useful for products to be placed in harsh environments, such as the ureter.

The functional groups of the copolymers of the present invention are attached in a pendant fashion (i.e. to a side chain of the copolymer). This means that the active groups will normally be available on the surface of the copolymer, where they will be able to effectively perform their function.

The pendant groups are incorporated into the polymer structure during the initial polymerization process. Therefore, the pendant groups are covalently bound to the polymer backbone and will typically remain adhered to the polymer on exposure to normal blood flow. Furthermore, since no post-polymerization attachment means are required, alterations in the mechanical properties of the polymer can generally be avoided.

The incorporation of the pendant groups into the polymer structure during initial polymerization also promotes an even distribution of the active groups throughout the entire polymer. Furthermore, only small amounts of the active group are required since the covalent binding of the group to the copolymer reduces the possibility of the active group washing away from the polymer surface. This is particularly advantageous when the active group to be bound to the copolymer surface is an expensive material, for example a growth factor peptide.

Thus, in one embodiment, by selection of suitable pendant groups the present invention provides copolymers having good biological properties which are highly bio-stable and show good compatibility with blood. The polymers can also enhance non-thrombogenicity and interfere with platelet aggregation close to the polymer surface. Furthermore, the polymers may have similar mechanical properties to that of the basic polymer structure. In the case of polyol polyurethanes, the polymers may thus have similar mechanical properties to the basic polyolpolyurethane and may therefore have high tensile strength and tear resistance. The enhanced mechanical and biological properties of the copolymers of the invention renders them useful for the production of implantable devices such as vascular grafts, dialysis shunts and heart valves.

In a preferred embodiment, the present invention provides a copolymer comprising (a) one or more pendant siloxane segments and (b) one or more polyol segments, wherein at least a part of each of said pendant siloxane segment(s) is on a side chain of the copolymer. Typically, each of said segments is linked to one or more further segments, which may be the same or different, via urea or urethane linkages.

The copolymers of this embodiment of the invention have good biological properties. They are highly biostable and show good compatibility with blood. The presence of the siloxane groups on side chains of the copolymer enhances non-thrombogenicity. The siloxanes interfere with platelet aggregation close to the polymer surface and therefore reduce blood coagulation on the surface. Furthermore, endothelial cells have been shown to grow on the polymer surface very effectively.

The presence of the siloxane groups on the side chain of the copolymer means that the beneficial mechanical properties of the basic polymer structure (preferably a polyol polyurethane) are retained. The inventors believe that the polymers of this embodiment of the invention therefore have high tensile strength and tear resistance.

The copolymers of the invention which incorporate siloxane groups are also useful in areas where visual properties are important, since they have a high transparency and discolour very slowly with age. For example, the copolymers are useful as ocular implants and contact lenses, or in non-biological applications such as transparent screens or coverings.

In a further embodiment of the invention, the siloxane group is a silsesquioxane cage which is bonded to the copolymer backbone via a pendant arm. These copolymers are particularly advantageous in terms of their mechanical properties, in particular in terms of their fatigue and crack resistance. The copolymers have the ability to divide the force of impact, or that of an enforced flex in the copolymer, into many smaller interactions involving the numerous individual silsesquioxane cages. Therefore, as a crack starts travelling through the copolymer material it breaks up into finer and finer cracks until the material has dissipated the energy required for crack growth. Fatigue occurs due to crack propagation and the fatigue resistance of the copolymers is therefore also improved.

Further, due to the nano-scale size and nature of the silsesquioxane cage, the cage structure contains no cracks or flaws. The silsesquioxane cage therefore does not introduce weakness into the copolymer chain. In contrast, linear polysiloxanes may themselves contain cracks, boundaries, dislocations or other flaws, leading to an inherent weakness in the copolymer structure.

Environmental stress cracking has been cited as being involved in the process of biodegradation. The reduction in cracking therefore provides the copolymers of the invention with improved biostability. Improved chemical resistance is a further benefit of the enhanced crack resistance.

The silsesquioxane containing copolymers have a high surface area compared to their weight. Stresses transferred over the surface of the copolymer can be dissipated due to the high surface area available. This factor may further increase the tensile strength and tear resistance of the copolymers.

The silsesquioxane-containing copolymers also display improved dimensional stability and stiffness. The presence of silsesquioxane cages on side chains of the copolymer reduces the possibility of the copolymer changing shape. The energy required for a change in shape, for example to bring a particular section of the copolymer chain to the surface, is increased. This causes an "anchoring" effect, reducing the ability of the copolymer to rearrange and restricting segmental motion.

The anchoring effect in turn aids both chemical resistance and biodurability, as well as dimensional stability. Solubility and ingress of lipids is controlled by segmental motion. Typically, as a polymer moves, it creates voids which can be filled by molecules such as lipids. These molecules then diffuse further into the structure of the polymer by filling successive sites. The restriction in segmental motion of the polymer therefore hinders ingress, which in turn increases the dimensional stability of the copolymer.

A further notable property of the copolymers of this embodiment of the invention is their ability to act as electron attractors, due to the electron withdrawing properties of the silsesquioxane cages. The silsesquioxane-containing copolymers of the invention may therefore also be suitable for use in fine-tuning the electronic band gap in conjugated polymer chains, and possibly for use with electrically conducting materials.

The silsesquioxane cages are classified as inorganic materials and the copolymers of this embodiment of the invention are therefore examples of inorganic polymers, typically inorganic polyurethanes.

In a further embodiment, the invention provides siloxane-containing copolymers which have a small proportion of siloxane groups compared with the number of polyol groups. For example, the ratio of siloxane-containing segments: polyol segments is typically less than 1:10, preferably less than 1:25. An excess of siloxane groups leads to a polymer which is highly compatible with blood, but the ability of cells to grow on the copolymer surface may be reduced. In contrast, copolymers containing a small proportion of siloxane groups still have a significant presence of siloxane on the surface leading to good blood compatibility, but the siloxane group presence is not detrimental to the growth of cells on the copolymer surface.

The present invention also provides a process for producing the copolymers of the invention, the process comprising polymerising, in any order, (i) one or more pendant group segments, the or each segment being bonded to at least one group selected from primary or secondary amine, hydroxyl and carboxylic acid groups;

(ii) a polyol;

(iii) an aromatic compound having two or more isocyanate groups; and optionally (iv) one or more chain extenders selected from amino acids, peptides, polypeptides and $C_1$-$C_6$ aliphatic groups, each of which has at least one substituent selected from primary or secondary amine, hydroxyl and carboxylic acid groups.

The invention also provides a process for lining the copolymers of the invention, the process comprising seeding endothelial cells onto the surface of a copolymer of the invention. Also provided are lined polymers obtained or obtainable by this process.

The invention also provides moulded articles, in particular implantable devices, typically for use in the replacement of a body part, comprising the copolymers or lined copolymers of the invention. An implantable device is a device suitable for implanting into, or surgically attaching to, a human or animal body. An implantable device is typically a prosthesis.

Finally, the invention provides a method of treating a human or animal patient in need of the replacement of a body part, said method comprising replacing said body part with an implantable device of the invention.

BRIEF DESCRIPTION OF THE FIGURES

FIG. 2 depicts an example of a silsesquioxane having 12 silicon atoms.

DETAILED DESCRIPTION OF THE INVENTION

Figure 1A:
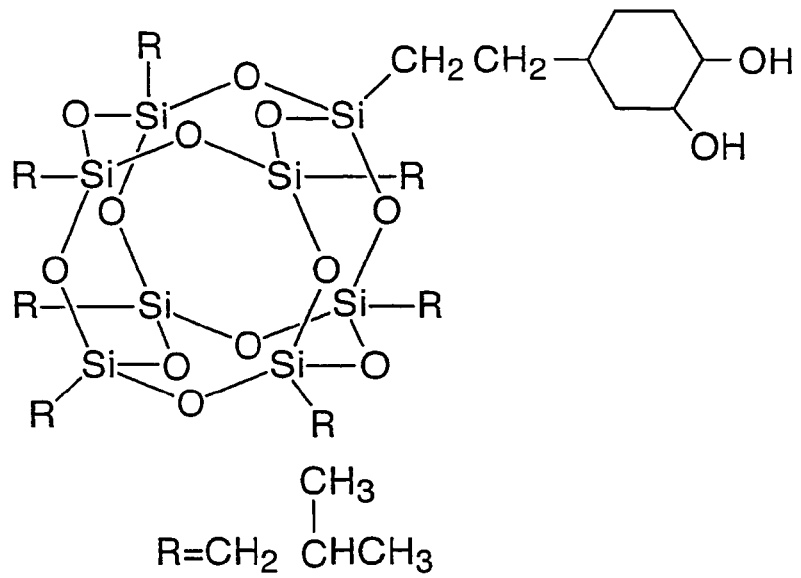
FIG. 1 depicts the structures of six different silsesquioxanes which can be used in the manufacture of the copolymers of the invention.
Figure 1B:
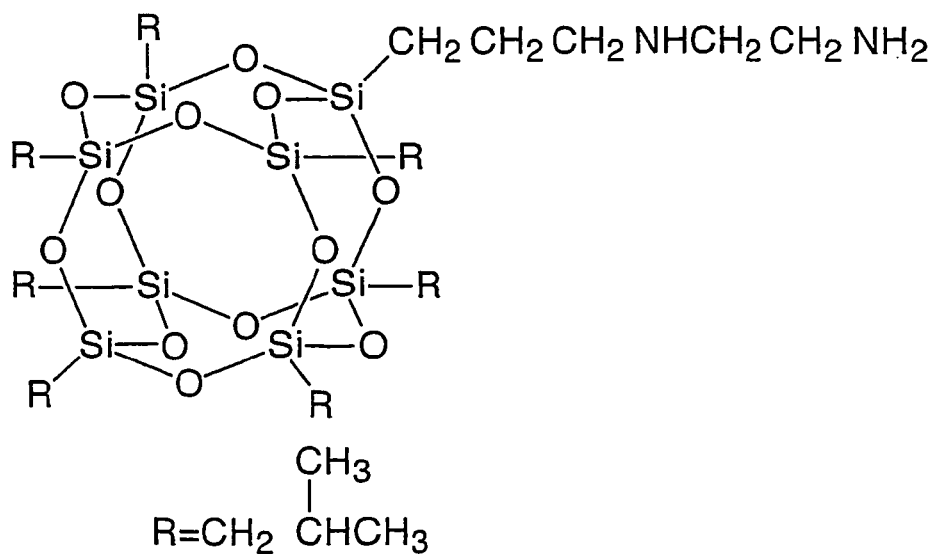
Figure 1C:
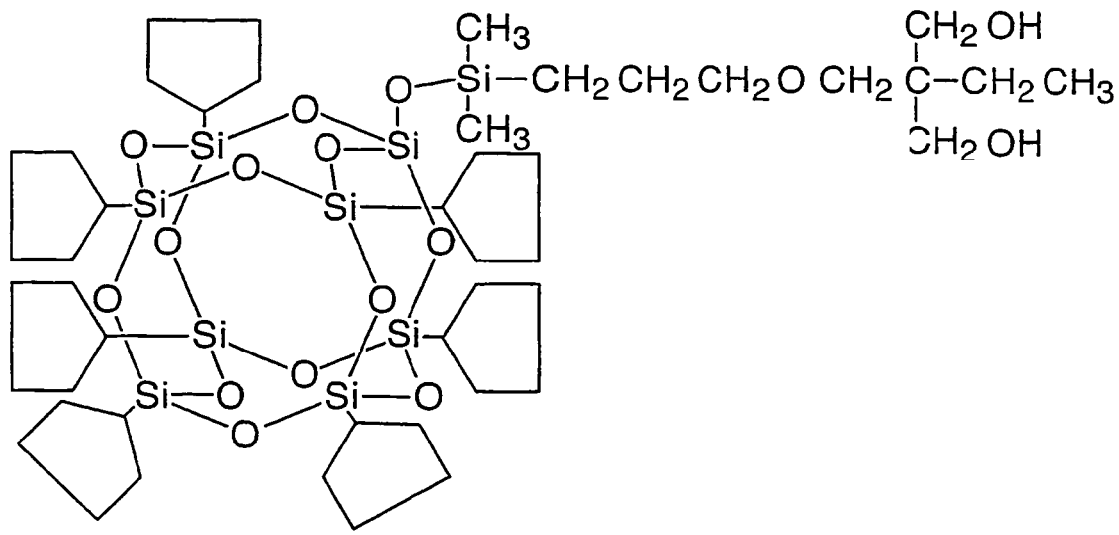
Figure 1D:
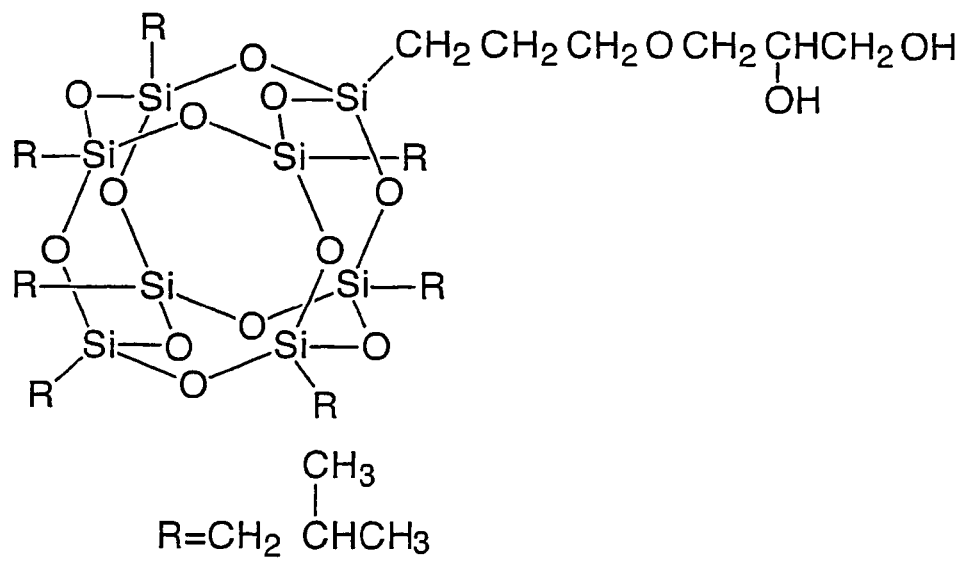

As used herein, an alkyl group or moiety is typically a $C_1$-$C_{12}$, for example a $C_1$-$C_8$, $C_1$-$C_6$ or $C_1$-$C_4$, alkyl group or moiety which may be straight or branched. Examples of alkyl groups and moieties are methyl, ethyl, n-propyl, i-propyl, n-butyl, sec-butyl, t-butyl, ethylene, propylene, butylene, 2-methylpentylene, n-hexylene and n-octylene.

As used herein, an alkenyl group or moiety is typically a $C_2$-$C_8$, for example a $C_2$-$C_6$ or $C_2$-$C_4$, alkenyl group or moiety which may be straight or branched. Examples of alkenyl groups and moieties are ethenyl, n-propenyl, i-propenyl and n-butenyl, in particular ethenyl, n-propenyl, ethenylene and propenylene.

As used herein, an alkynyl group is typically a $C_2$-$C_6$, for example $C_2$-$C_4$, alkynyl group which may be straight or branched. Examples of alkynyl groups are ethynyl, propynyl and n-butynyl, in particular ethynyl and propynyl.

An alkyl, alkenyl or alkynyl group or moiety may be unsubstituted or substituted with one or more, for example 1, 2 or 3 substituents. Examples of substituents include halogen atoms, hydroxyl, trifluoromethyl, $C_1$-$C_4$ alkoxy and $C_1$-$C_4$ alkylthio groups and groups of formula —NR$^1$R$^2$ wherein R$^1$ and R$^2$ are the same or different and are selected from hydrogen and $C_1$-$C_4$ alkyl groups. Preferred substituents include halogen atoms and hydroxyl, methyl, ethyl, methoxy, ethoxy, methylthio and dimethylamino groups. The substituents are themselves unsubstituted.

As used herein, a cycloalkyl group or moiety is typically a $C_3$-$C_{10}$ cycloalkyl group or moiety which may be a single ring or fused ring system. Examples of cycloalkyl groups and moieties are $C_3$-$C_6$ cycloalkyl groups and moieties, in particular cyclopentlyl, cyclohexyl, cyclopentylene and cyclohexylene.

A cycloalkyl group may be unsubstituted or substituted with one or more, for example 1, 2, 3 or 4 substituents. Examples of substituents on a cycloalkyl group include halogen atoms, hydroxyl, trifluoromethyl, $C_1$-$C_4$ alkyl, $C_1$-$C_4$ alkoxy and $C_1$-$C_4$ alkylthio groups, nitro groups and groups of formula —NR$^1$R$^2$ wherein R$^1$ and R$^2$ are the same or different and are selected from hydrogen and $C_1$-$C_4$ alkyl groups, for example halogen atoms, hydroxyl, trifluoromethyl, $C_1$-$C_4$ alkyl, $C_1$-$C_4$ alkoxy and $C_1$-$C_4$ alkylthio groups and groups of formula —NR$^1$R$^2$ wherein R$^1$ and R$^2$ are the same or different and are selected from hydrogen and $C_1$-$C_4$ alkyl groups. Preferred substituents include halogen atoms and hydroxyl, methyl, ethyl, methoxy, ethoxy, methylthio, nitro and dimethylamino groups, for example halogen atoms and hydroxyl, methyl, ethyl, methoxy, ethoxy, methylthio and dimethylamino groups. The substituents are themselves unsubstituted.

As used herein an aryl group is typically a $C_6$-$C_{10}$ aryl group which may be a single ring or fused ring system. Examples of aryl groups are phenyl and naphthyl.

An aryl group may be unsubstituted or substituted with one or more, for example 1, 2 or 3 substituents. Examples of substituents on an aryl group include halogen atoms, $C_1$-$C_4$ alkyl, $C_1$-$C_4$ alkoxy and $C_1$-$C_4$ alkylthio groups and groups of formula —NR$^1$R$^2$ wherein R$^1$ and R$^2$ are the same or different and are selected from hydrogen and $C_1$-$C_4$ alkyl groups. Preferred substituents include methyl, ethyl, methoxy, methylthio and dimethylamino groups. The substituents are themselves unsubstituted.

As used herein, an alkoxy group is typically an alkyl group as defined above which is bonded to an oxygen atom. An alkylthio group is typically an alkyl group as defined above which is bonded to a sulfur atom. Alkoxy and alkylthio groups are typically unsubstituted.

As used herein, a heteroaryl group is typically a 5- to 10-membered heteroaryl group containing from 1 to 5 heteroatoms selected from nitrogen, oxygen and sulfur atoms. A heteroaryl group typically comprises from 1 to 5, for example from 1 to 4, nitrogen atoms. Preferred examples of heteroaryl groups include pyridine, pyrazole, purine, pyrimidine and derivatives therefore, for example, purine and pyrimidine and derivatives thereof.

A heteroaryl group may be unsubstituted or substituted with one or more, for example 1, 2 or 3 substituents. Examples of substituents on a heteroaryl group include halogen atoms, carboxy, oxy, $C_1$-$C_4$ allyl, $C_1$-$C_4$ alkoxy and $C_1$-$C_4$ alkylthio groups and groups of formula —NR$^1$R$^2$ wherein R$^1$ and R$^2$ are the same or different and are selected from hydrogen and $C_1$-$C_4$ alkyl groups. Preferred substituents include methyl, ethyl, amino, carboxy and oxy groups. The substituents are themselves unsubstituted.

As used herein, a heterocyclyl group is typically a 5- to 6-membered heterocyclyl group containing from 1 to 3 heteroatoms selected from nitrogen, oxygen and sulfur atoms which is optionally bonded to a further ring, for example a phenyl ring. Examples of heterocyclyl groups include phthalanyl, tetrahydrofuranyl pyrrolyl, piperidinyl, morpholinyl tetrahydropyranyl and tetrahydrothienyl, in particular tetrahydrofuranyl.

A heterocyclyl group may be unsubstituted or substituted with one or more, for example 1, 2 or 3 substituents. Examples of substituents on a heterocyclyl group include halogen atoms, hydroxyl, carboxy, oxy, $C_1$-$C_4$ alkyl which is optionally substituted with hydroxyl, $C_1$-$C_4$ alkoxy and $C_1$-$C_4$ alkylthio groups, phenyl and groups of formula —$NR^1R^2$ wherein $R^1$ and $R^2$ are the same or different and are selected from hydrogen and $C_1$-$C_4$ alkyl groups. Preferred substituents include hydroxyl groups. A phenyl substituent may be further substituted with halogen or unsubstituted $C_1$-$C_4$ alkyl, $C_1$-$C_4$ alkoxy or —$NR^1R^2$ groups. The remaining substituents are themselves unsubstituted, except as indicated.

The copolymers of the invention comprise one or more pendant group segments selected from the segments (i) to (v) as defined above. The term "pendant group segment" means that at least a part of the segment is on a side chain of the copolymer. In one embodiment of the invention, two or more different types of pendant group segment selected from segments (i) to (v) are included in the polymer. For example, a siloxane (e.g. silsesquioxane or partial cage silsesquioxane) segment as well as one or more of segments (ii) to (v) may be used.

The pendant group segments optionally comprise a pendant arm to attach the functional part of the pendant group segment to the polymer backbone. In this case, the functional part of the segment will be on a side chain of the copolymer, whilst at least a part of the pendant arm is in the backbone of the copolymer. The term "in the backbone of the copolymer" includes the situation in which the pendant arm is attached to the end of the copolymer chain (the pendant group segment is a chain terminating group). Preferred pendant arms which can be used in the present invention are further defined below.

The siloxane segments may comprise linear siloxanes, cage-like silsesquioxanes or partial cage siloxanes. Where more than one siloxane segment is present in a copolymer of the invention, each siloxane segment may be the same or different. Typically, the copolymer comprises one siloxane segment selected from those comprising linear siloxanes, cage-like silsesquioxanes and partial cage siloxanes.

A linear siloxane typically comprises repeating units of the formula

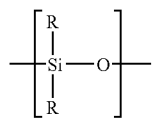

wherein each R is the same or different and represents an aliphatic or aromatic group. Typically, each R is the same or different and represents an alkyl, alkenyl, alkynyl, siloxy, cycloalkyl or aryl group, for example an alkyl, alkenyl, alkynyl, cycloalkyl or aryl group. Preferably, each R represents an alkyl group or phenyl group, in particular an alkyl group.

Preferred alkyl groups are $C_1$-$C_6$, for example $C_1$-$C_4$, alkyl groups which may be straight or branched. Examples of suitable alkyl groups are methyl, ethyl, n-propyl, i-propyl, n-butyl and t-butyl in particular methyl and ethyl preferably methyl.

Preferred alkenyl groups are $C_2$-$C_6$, for example $C_2$-$C_4$, alkenyl groups which may be straight or branched. Examples of suitable alkenyl groups are ethenyl, n-propenyl, i-propenyl and n-butenyl, in particular ethenyl and n-propenyl.

Preferred siloxy groups are those of formula —$OSiR^{11}_3$, wherein each $R^{11}$ is the same or different and is selected from hydrogen and $C_{1-4}$, typically $C_{1-2}$ alkyl groups.

Preferred alkynyl groups are $C_2$-$C_6$, for example $C_2$-$C_4$, alkynyl groups which may be straight or branched. Examples of suitable alkynyl groups are ethynyl, propynyl and n-butynyl, in particular ethynyl and propynyl.

Preferred cycloalkyl groups are $C_3$-$C_{10}$ cycloalkyl groups including single ring and fused ring systems. Examples of suitable cycloalkyl groups are $C_3$-$C_6$ cycloalkyl groups, in particular cyclohexyl and cyclopentyl.

Preferred aryl groups are $C_6$-$C_{10}$-aryl groups including single ring and fused ring systems. Examples of suitable aryl groups are phenyl and naphthyl.

The groups R may be unsubstituted or substituted with one or more, for example 1, 2 or 3 substituents. Examples of suitable substituents include halogen atoms, $C_1$-$C_4$ alkyl, $C_1$-$C_4$ alkoxy and $C_1$-$C_4$ alkylthio groups and groups of formula —$NR^1R^2$ wherein $R^1$ and $R^2$ are the same or different and are selected from $C_1$-$C_4$ alkyl groups. Preferred substituents include methyl, ethyl, methoxy, methylthio and dimethylamino groups. Preferably R is unsubstituted.

The terminal end of the linear siloxane (that which is not bound to the polyurethane backbone) is typically linked to a further group R, which may be the same or different from the groups R in the repeating units.

Preferred linear siloxanes have a molecular weight of up to 5000, preferably up to 2000, more preferably up to 1000. The present inventors have found that by reducing the molecular weight of the polysiloxane-containing segment, the ability of cells to adhere to the polymer surface is improved. This improvement is achieved whilst still retaining good compatibility with blood.

The linear siloxanes (i.e. the functional part of a linear siloxane segment) may be attached to the backbone of the polymer either directly or via a pendant arm. Typically, the linear siloxane is directly-attached to the backbone. For example, the siloxane may be bound to a polyurethane backbone by a bond to a nitrogen atom of a urethane or urea linkage. However, any alternative means of attachment may also be used.

In one embodiment of the invention, the siloxane group is attached to the polymer via a pendant arm. Where a pendant arm is used, the siloxane group is on a side chain of the copolymer, whilst at least a part of the pendant arm is in the backbone of the copolymer. Where the siloxane is a silsesquioxane cage or partial cage, a pendant arm is typically used.

In this embodiment of the invention, the pendant siloxane segment typically has the structure

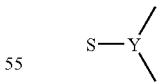

wherein S is a siloxane group and Y is a pendant arm. Typically, Y is an aliphatic group which is bonded to at least two further segments in the polymer, e.g. via urea or urethane linkages.

The siloxane group S may be a linear siloxane having the structure set out above. Alternatively, the group S may be a silsesquioxane cage or partial cage. Where S is a silsesquioxane cage, it typically consists of repeating units of formula

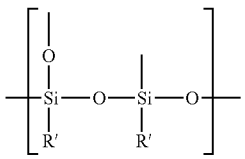

wherein each R' is the same or different and represents an aliphatic or aromatic group, and wherein one R' group is replaced with a bond attached to group Y. Typically, each R' is the same or different and represents an alkyl, alkenyl, alkynyl, siloxy, cycloalkyl or aryl group, for example an alkyl, alkenyl, alkynyl, cycloalkyl or aryl group. Preferably each R' is the same.

Preferred alkyl groups are $C_1$-$C_6$, for example $C_1$-$C_4$, alkyl groups which may be straight or branched. Examples of suitable alkyl groups are methyl, ethyl, n-propyl, i-propyl, n-butyl, sec-butyl and t-butyl, in particular sec-butyl.

Preferred alkenyl, alkynyl, siloxy, cycloalkyl and aryl groups are as defined for R above. Preferably, R' is alkyl, siloxy, cycloalkyl or aryl, for example alkyl, cycloalkyl or aryl. Most preferably, R' is $C_1$-$C_4$ alkyl, $-OSiR^{11}_3$ wherein each $R^{11}$ is the same or different and is hydrogen or methyl, cyclohexyl, cyclopentyl or phenyl, for example R' may be $C_1$-$C_4$ alkyl, cyclohexyl, cyclopentyl or phenyl.

The groups R' may be unsubstituted or substituted with one or more, for example 1, 2 or 3 substituents. Examples of suitable substituents are those set out above as suitable substituents for R. Preferably R' is unsubstituted.

The structure of the silsesquioxane cage is not particularly limited and any available cages can be used. Preferred cages are those containing 8 silicon atoms and 12 oxygen atoms, having a formula $-(Si_8O_{12}R'_7)$, or those having 12 silicon atoms and 18 oxygen atoms having a formula $-(Si_{12}O_{18}R'_{11})$, wherein R' is as defined above. An example of a silsesquioxane cage having 12 silicon atoms is depicted in FIG. 2. Further examples of silsesquioxane cages are depicted in FIG. 1.

Alternative examples are the silsesquioxane groups present in the following compounds: 1,3,5,7,9,11,13-heptacyclopentyl-15-glycidylpentacyclo[9.5.1.1$^{3,9}$.1$^{5,15}$.1$^{7,13}$]-octasiloxane; 3,5,7,9,11,13,15-heptacyclopentylpentacyclo[9.5.1.1$^{3,}$ $^{9}$.1$^{5,15}$.1$^{7,13}$]octasiloxan-1-ol; (Glycidoxypropyldimethylsilyloxy)-heptacyclopentylpentacyclooctasiloxane; 1,3,5,7,9,11,13,15-octakis(dimethylsilyloxy)pentacyclo[9.5.1.1$^{3,9}$.1$^{5,15}$.1$^{7,13}$]-octasiloxane; 3-(3,5,7,9,11,13,15-heptacyclopentylpentacyclo[9.5.1.1$^{3,9}$.1$^{5,15}$.1$^{7,}$ $^{13}$]octasiloxan-1-yl)propyl methacrylate; 1-(4-Vinylphenyl)-3,5,7,9,11,13,15-heptacyclopentylpentacyclo-[9.5.1.1$^{3,9}$.1$^{5,}$ $_{15}$.1$^{7,13}$]octasiloxane; 1-Vinyl-3,5,7,11,13,15-isobutylpentacyclo[9.5.1.1(3,9).1(5,15).1(7,13)]-octasiloxane; and 1-[2-(3,4-Epoxycyclohexyl)ethyl]-3,5,7,9,11,13,15-heptacyclopentylpentacyclo-[9.5.1.1(3,9).1(5,15).1(7,13)]octasiloxane.

The properties of the final copolymer can be adapted by changing the silsesquioxane cage, in particular by adapting the R' groups on the silsesquioxane cage. For example, the use of larger groups such as cyclohexyl or cyclopentyl groups at the position R' leads to a copolymer having increased stiffness and dimensional stability. Such a copolymer might be suitable for use in prostheses where dimensional stability is important, such as heart valves. Alternatively, the use of smaller R' groups such as $C_1$-$C_4$ alkyl groups might provide a more flexible copolymer which is, for example, useful in making vascular grafts.

The silsesquioxane cage is attached to a pendant arm via one of the silicon atoms. The pendant arm is in turn attached to the polymer (typically polyurethane) backbone. Typical structures for the pendant arm are described below.

Figure 3:
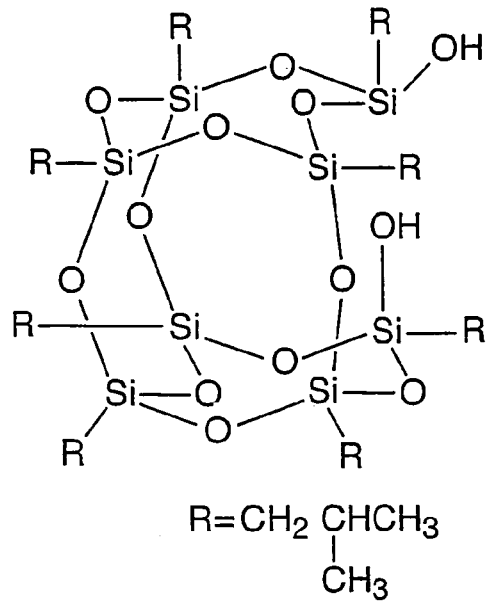
FIG. 3 depicts an example of a partial silsesquioxane cage.

When the siloxane group S is a partial silsesquioxane cage, the partial cage is typically a silsesquioxane cage as described above in which one or more of the atoms and bonds forming the cage is missing, such that a partial cage structure is formed. An example of such a structure is depicted in FIG. 3. However, alternative partial cage structures may also be used including the partial cage groups present in 1,3,5,7,9,11,14-heptacyclohexyltricyclo[7.3.3.1$^{5,11}$]heptasiloxane-3,7,14-triol; 1,3,5,7,9,11,14-heptacyclopentyltricyclo[7.3.3.1$^{5,11}$]heptasiloxane-endo-3,7,14-triol; 3',5'-O-(1,1,3,3-tetraisopropyl-1,3-disiloxandiyl)-adenosine and 3',5'-O-(1,13,3-tetraisopropyl-1,3-disiloxandiyl)cytidine. As depicted above, the partial cage is bonded to a pendant arm Y. The typical structures of a pendant arm Y are described below.

Preferred pendant siloxane segments have a molecular weight of up to 5000, preferably up to 2000, more preferably up to 1000. The present inventors have found that by reducing the molecular weight of the pendant siloxane segment, the ability of cells to adhere to the polymer surface is improved. This improvement is achieved whilst still retaining good compatibility with blood.

The copolymers of the invention comprising pendant silsesquioxane or partial cage silsesquioxane segments are particularly tough and tear resistant. Thus the copolymers have a high viscosity, for example of 10,000 cp or more, preferably 100,000 cp or more.

The copolymers of the invention may comprise one or more segments containing phosphoryl choline or a derivative or analogue thereof. The phosphoryl choline or derivative or analogue thereof is attached to the polymer backbone via a pendant arm. The pendant arm may be a methylene group or a longer pendant arm, e.g. those defined below.

The segments comprising phosphoryl choline or a derivative thereof typically have the formula (V)

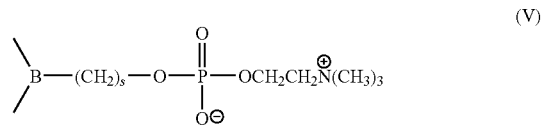

(V)

wherein s is 0, 1, 2, 3 or 4, typically 0 or 1. The $O^{31}$ group of the phosphoryl choline is optionally bound to the group B to form a ring.

The group B is typically attached to two (or optionally one or three) further segments (e.g. via urea or urethane groups) in the copolymer. The group B is, for example, a pendant arm as defined below. In one embodiment, the group B is a group of formula

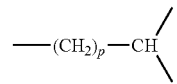

wherein p is an integer of 0 to 8, preferably 1 to 8. B is preferably an ethylenyl or propylenyl group, for example an ethylenyl group.

In an alternative embodiment, the group B comprises a 5- to 10-membered heterocyclyl or heteroaryl group containing from 1 to 5 heteroatoms selected from nitrogen, oxygen and sulfur atoms. B typically contains a heteroaryl group. The heteroaryl group typically comprises from 1 to 5, for example from 1 to 4, nitrogen atoms. Preferred examples of heteroaryl groups include purine and pyrimidine and derivatives thereof including the purine derivatives adenine(6-amino purine), guanine(2-amino-6-oxy purine), hypoxanthine(6-oxy purine) and xanthine(2,6-dioxy purine), and the pyrimidine derivatives uracil(2,4-dioxy pyrimidine), thymine(2,4-dioxy-5-methyl pyrimidine), cytosine(2-oxy-4-amino pyrimidine) and orotic acid(2,4-dioxy-6-carboxy pyrimidine). An example of a heterocyclyl group is a phalanyl derivative.

In this embodiment, the group B is preferably a group of formula (VI) or (VIA) shown below. In formula (VI), $(B_1)_q$ is attached to the phosphoryl choline group and $(B_3)_m$ is attached to two (or optionally one or three) further segments (e.g. via urea or urethane groups) in the copolymer. In formula (VIA), this order of attachment is reversed such that $(B_3)_m$ is attached to the phosphoryl choline group and $(B_1)_q$ is attached to two (or optionally one or three) further segments in the copolymer.

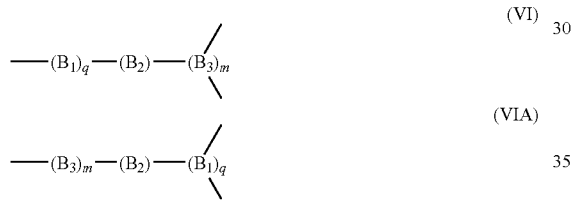

Each $B_1$ is the same or different and is a $C_6$-$C_{10}$ aryl, $C_1$-$C_8$ alkylene, $C_2$-$C_8$ alkenylene, $C_3$-$C_6$ cycloalkyl group or a 5- or 6-membered heterocyclyl group containing 1, 2 or 3 heteroatoms selected from nitrogen, oxygen and sulfur; $B_2$ is a 5- to 10-membered heterocyclyl or heteroaryl group containing from 1 to 5 heteroatoms selected from nitrogen, oxygen and sulfur, typically a heterocyclyl or heteroaryl group as defined in the above paragraph; $B_3$ is a pendant arm as defined below; q is 0, 1, 2 or 3; and m is 0 or 1. When m is 0 in formula (VI), the heteroaryl group $B_2$ is directly attached to two (or optionally one or three) further segments in the copolymer. When m is 0 in formula (VIA), the group $B_2$ is directly attached to the phosphoryl choline group.

$B_1$ is preferably phenyl, a $C_1$-$C_4$ alkylene group, a $C_5$-$C_6$ cycloalkyl group or a 5- or 6-membered heterocyclyl group containing 1, 2 or 3 heteroatoms selected from nitrogen, oxygen and sulfur. The or each group $B_1$ is, independently, unsubstituted or substituted with 1, 2, 3 or 4 substituents. The substituents are typically selected from halogen atoms, in particular chlorine and bromine atoms, hydroxy groups, $C_1$-$C_4$ alkyl groups which are optionally substituted with hydroxyl groups, $C_1$-$C_4$ alkoxy groups, phenyl groups and groups of formula —$NR^1R^2$ wherein $R^1$ and $R^2$ are independently selected from H and $C_1$-$C_4$ alkyl groups. Phenyl substituents may themselves be substituted, for example with $C_{1-4}$ alkyl, $C_{1-4}$ alkoxy, hydroxyl, halogen or —$NR^1R^2$, but are not substituted with further phenyl groups. Preferred substituents are chlorine, bromine, hydroxyl, $C_1$-$C_2$ alkyl, hydroxymethyl and $C_1$-$C_2$ alkoxy.

$B_2$ is preferably a heteroaryl group as defined above. q is preferably 1 or 2. m is preferably 0.

Examples of preferred groups B of formula (VI) or (VIA) are those derived from the purine and pyrimidine containing bases which are found in DNA and RNA (e.g. adenine, guanine, cytosine, thymine and uracil). Particularly preferred are cytidinyl, adenosinyl and guanosinyl groups and deoxycytidinyl, deoxyadenosinyl and deoxyguanosinyl groups. Each of these groups is optionally attached to a pendant arm $B_3$. Where no pendant arm is used, the groups may be directly attached to the polymer, for example via the —N=C(NH$_2$)— group present on the purine or pyrimidine ring of a cytidine or adenosine group respectively.

Where the group B comprises a purine or pyrimidine group or a derivative thereof, the phosphoryl choline group may impart to the copolymer both the blood compatibility properties derived from the phosphoryl choline part of the segment, but also non-thrombogenic and possibly anti-microbial properties derived from the purine or pyrimidine part of the segment. Where anti-microbial properties are imparted, the copolymers produced may have an aseptic surface which is particularly useful for products to be used in the ureter.

The segments comprising an analogue of phosphoryl choline typically comprise one or more linked phosphate groups, for example a monophosphate or triphosphate group. Thus, preferred segments comprising an analogue of phosphoryl choline have the formula (VII)

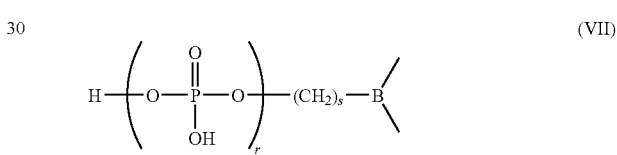

wherein s and B are as defined above with regard to the phosphoryl choline or derivatives thereof, r is 1, 2, 3, 4 or 5, preferably 1 or 3 and one or more of the —OH groups on the phosphate group(s) may be in the form of a salt, i.e. a group —$O^-M^+$ wherein $M^+$ is a cation, for example a sodium, potassium or ammonium ion. One or more OH groups of the phosphate groups(s) may be bound to the group B to form a ring.

The segments comprising phosphoryl choline or derivatives or analogues thereof may be derived from the following compounds:
2'-Deoxyadenosine-5'-monophosphoric acid,
2'-Deoxycytidine-5'-monophosphoric acid,
2'-Deoxyguanosine 5'-monophosphate,
Cytidine 5'-triphosphate
Adenosine 2',3'-cyclic monophosphate
(−)-Adenosine 3',5'-cyclic monophosphate
Adenosine 5'-triphosphate
Thymolphthalein monophosphoric acid Alternative pendant group segments which may be employed in the polymers of the invention, either alone or in combination with other pendant group segments, are segments containing a purine or pyrimidine group or a derivative thereof. Examples of such segments are those including the purine derivatives adenine(6-amino purine), guanine(2-amino-6-oxy purine), hypoxanthine(6-oxy purine) and xanthine(2,6-dioxy purine), and the pyrimidine derivatives uracil (2,4-dioxy pyrimidine), thymine(2,4-dioxy-5-methyl pyrimidine), cytosine(2-oxy-4-amino pyrimidine) and orotic acid(2,4-dioxy-6-carboxy pyrimidine). Particularly preferred are cytidinyl, adenosinyl and guanosinyl groups and deoxycytidinyl, deoxyadenosinyl and deoxyguanosinyl groups. A particular example of such a segment is that derived from (−)-3',5'-O-(1,1,3,3-tetraisopropyl-1,3-disiloxanediyl)adenosine.

Polymers comprising these segments may have particularly good non-thrombogenic and anti-microbial properties. The copolymers may therefore have an aseptic surface and thus be useful for products to be used in the ureter.

The copolymers of the present invention may comprise one or more segments containing a di- or trifluoromethyl group, preferably a trifluoromethyl group. The structure of these segments is not particularly limited, as long as one or more di- or trifluromethyl groups is present. In one embodiment, the di- or trifluoromethyl group may be present on a siloxane segment, on a segment containing phosphoryl choline or a derivative or analogue thereof, or on a segment of formula (XII) or formula (I). Examples of segments comprising trifluoromethyl groups and siloxane groups are those derived from the compounds depicted in FIG. 4.

In an alternative embodiment, the di- or trifluoromethyl group is present on a separate segment. This segment will typically comprise one or more di- or trifluoromethyl groups but will not comprise any further groups which impart functionality to the final polymer. For example, the di- or trifluromethyl containing segment may be a straight or branched, $C_2$-$C_{12}$, for example $C_4$-$C_8$, alkylene group which is substituted with one or more di- or trifluromethyl groups and optionally one or more additional substituents. The additional substituents are typically selected from halogen atoms, hydroxyl groups, $C_1$-$C_4$ alkoxy groups and groups of formula —$NR^1R^2$ wherein $R^1$ and $R^2$ are independently selected from hydrogen and $C_1$-$C_4$ alkyl groups. Preferred substituents are fluorine, chlorine, bromine and hydroxyl, in particular fluorine. The alkylene group is bonded to two (or optionally one or three) further segments (e.g. via urea or urethane groups) in the copolymer backbone. Preferred di- or tri-fluoromethyl containing groups are highly fluorinated alkylene groups.

Typically a di- or trifluoromethyl containing segment is a group of formula (VII)

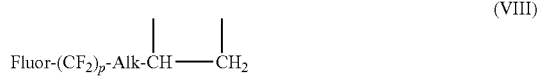

(VIII)

wherein Alk is a $C_1$-$C_4$, for example $C_1$-$C_2$, alkylene group or a group —$(CH_2)_m$—O—$(CH_2)_n$—, wherein m and n are each individually 0, 1 or 2, p is from 0 to 12 and fluor is —$CF_3$ or a group —$CF_xH_y(CF_3)_z$ wherein each of x and z is 0, 1 or 2; y is 0 or 1; and x+y+z=3. Preferably Alk is $CH_2$ or $CH_2$—O—$CH_2$. Preferably p is from 2 to 9. Preferably Fluor is —$CF_3$, —$C(CF_3)_2F$ or —$CHF_2$, most preferably —$CF_3$ or −$C(CF_3)_2F$.

Segments comprising di- or trifluoromethyl groups may be derived from the following compounds:
[2,2,3,3,4,4,5,5,6,7,7,7-Dodecafluoro-6-(trifluoromethyl)heptyl]oxirane,
(2,2,3,3,4,4,5,5,6,6,7,7,8,8,9,9,10,10,11,11,11-Heneicosafluoroundecyl)oxirane,
(2,2,3,3,4,4,5,5,6,6,7,7,8,8,9,9,9-Heptadecafluorononyl)oxirane,
(2,2,3,3,4,4,5,5,6,6,7,7,8,8,9,9,9-hexadecafluoro-8-(trifluoromethyl)nonyl]oxirane,
[2,2,3,3,4,5,5,5-octafluoro-4-(trifluoromethyl)pentyl]oxirane,
Glycidyl 2,2,3,3,4,4,5,5,6,6,7,7-dodecafluoroheptyl ether,
Glycidyl 2,2,3,3,4,4,5,5,6,6,7,7,8,8,9,9-hexadecafluorononyl ether, The copolymers of the invention may comprise one or more heparin-like segments containing a group of formula (XII)

wherein D is an aliphatic or aromatic group and Ar—$SO_3^-$ comprises one or more linked aryl and/or heteroaryl groups, at least one of the aryl and/or heteroaryl groups having an $SO_3^-$ substituent.

The heparin-like segments typically display blood compatibility properties substantially the same as those of heparin itself. Preferred heparin-like segments are in the form of a cage. The heparin-like segments are, for example, derived from Acid dyes, e.g. Acid Yellow or Acid Red, and typically comprise a —N=N— group and an aryl or heteroaryl group substituted with at least one $SO_3^-$ group.

The group of formula (XII) is typically directly attached to the polymer backbone. Thus, the segment typically is a group of formula (I) which is bonded to one or more, typically two, further segments, typically via urea or urethane groups. Alternatively, a pendant arm may be used to attach the group of formula (XII) to the backbone if desired. The group of formula (XII) is typically attached to the polymer or to a pendant arm via one or both of groups D and Ar.

The group Ar in the formula (XII) typically comprises one, two or three, preferably one or two, linked aryl and/or heteroaryl groups, each of which may be the same or different from one another. The aryl and/or heteroaryl groups are typically directly linked to one another. Preferred aryl groups are phenyl and naphthyl, in particular phenyl. Preferred heteroaryl groups are N-containing groups including pyridyl, pyrazolyl and pyrimidinyl, in particular pyrazolyl.

The group Ar is substituted with at least one $SO_3^-$ group. The $SO_3^-$ group is in the form of a salt or an acid, typically a salt. Preferred salts are salts with alkali or alkaline earth metals, in particular alkali metals, e.g. sodium. The group Ar may be further substituted with one or more, for example one, two or three further substituents. Examples of substituents include halogen atoms, $C_1$-$C_4$ alkyl, $C_1$-$C_4$ alkoxy and $C_1$-$C_4$ alkylthio groups, nitro groups and groups of formula —$NR^2$ wherein $R^1$ and $R^2$ are the same or different and are selected from $C_1$-$C_4$ alkyl groups. Preferred substituents include methyl, ethyl, methoxy, methylthio, nitro and dimethylamino groups. The substituents are themselves unsubstituted.

The group D- is typically a group $D^1$-$D^2$-$D^3$- wherein $D^3$ is attached to the N=N group. In this embodiment, $D^1$ is typically an aryl group or heteroaryl group, preferably an aryl group, for example phenyl. $D^2$ is a functional group selected from —NR'CO—, —CONR'—, —NR'CONR'—, —OCO—, —COO—, —OCOO—, —NR'SO₂—, —SO₂NR'—, —NR'SO₂NR'—, —OSO₂—, —SO₂O— or —OSO₂O—, preferably —NR'CO—, —CONR', —OCO—, —COO—, —NR'SO₂— or —SO₂NR'—, more preferably —NR'CO—, —CONR', —NR'SO₂— or —SO₂NR'—, wherein each R' is the same or different and is hydrogen or a $C_{1-4}$ alkyl group, e.g. a $C_{1-4}$ alkyl group. $D^3$ is an aliphatic or aromatic group, for example an aryl or heteroaryl group, or an alkylene or alkenylene group. Examples of aryl and heteroaryl groups are phenyl, naphthyl and pyridyl, in particular phenyl. Examples of alkylene and alkenylene groups are $C_{1-6}$ alkylene and $C_{2-6}$ alkenylene groups.

$D^1$ and $D^3$ may be unsubstituted or substituted with one, two or three substituents. Examples of substituents include halogen atoms, $C_1$-$C_4$ alkyl, $C_1$-$C_4$ alkoxy and $C_1$-$C_4$ alkylthio groups, nitro groups and groups of formula —NR$^1$R$^2$ wherein R$^1$ and R$^2$ are the same or different and are selected from $C_1$-$C_4$ alkyl groups. Preferred substituents include methyl, ethyl and methoxy groups. The substituents are themselves unsubstituted. Most preferred groups of formula (XII) are compounds in which Ar comprises one or two linked aryl or heteroaryl groups selected from phenyl and pyrazolyl, Ar being substituted with one or two —SO$_3$— groups and optionally one, two or three further substituents selected from methyl, ethyl, methoxy, methylthio, nitro and dimethylamino groups; and D is a group D$^1$-D$^2$-D$^3$- wherein D$^1$ is an aryl or heteroaryl group which is unsubstituted or substituted with one, two or three substituents selected from methyl, ethyl and methoxy groups, D$^2$ is —NR'CO—, —CONR', —OCO—, —COO—, —NR'SO$_2$— or —SO$_2$NR'— wherein each R' is the same or different and is hydrogen or a $C_{1-4}$ alkyl group, e.g. a $C_{1-4}$ alkyl group and D$^3$ is phenyl, $C_{1-4}$ alkylene or $C_2$-4 alkenylene which is unsubstituted or substituted with one, two or three substituents selected from methyl, ethyl and methoxy groups.

Preferably in this embodiment D$^1$ is phenyl which is unsubstituted or substituted with one, two or three substituents selected from methyl, ethyl and methoxy groups, D$^2$ is —NR'CO—, —CONR', —NR'SO$_2$— or —SO$_2$NR'— wherein each R' is the same or different and is hydrogen or a $C_{1-4}$ alkyl group, e.g. a $C_{1-4}$ alkyl group and D$^3$ is phenyl, $C_{1-4}$ alkylene or $C_{2-4}$ alkenylene which is unsubstituted or substituted with one, two or three substituents selected from methyl, ethyl and methoxy groups. Particularly preferred groups of formula (XII) are derivatives of Acid dyes, e.g. Acid Yellow compounds, in particular Acid Yellow 29, Acid Yellow 76 and Acid Yellow 99.

The copolymers of the invention may comprise one or more segments containing a group of formula (I) as set out above. The group of formula (I) is typically directly attached to the polymer backbone. Thus, the segment typically is a group of formula (I) which is bonded to one or more, typically two, further segments (e.g. via urea or urethane groups) in the copolymer. For example, the group of formula (I) may be attached to a urea or urethane group in the polymer backbone via the NH$_2$ group of the two lysine groups bonded to the Spacer.

A pendant arm may be used to attach the group of formula (I) to the backbone if desired. In this case, the pendant arm is typically attached to the —NH$_2$ group of one of the lysine groups bonded to the Spacer, in particular to the lysine group on the right hand side of the Spacer as depicted in formula (I). Alternative attachment locations, for example the —NH$_2$ group (or an —OH group) of other amino acids such as any amino acids present in the Spacer, can also be envisaged In this embodiment the pendant arm is typically a short aliphatic chain, e.g. a $C_2$-$C_4$ alkylene group which is unsubstituted or substituted as described below for the pendant arm. Preferred pendant arms are unsubstituted, e.g. ethylene.

In the formula (I), [A1] represents an inert amino acid. An inert amino acid is one which does not contain polymerisable groups (i.e. —NH$_2$ or —OH groups). Typically an inert amino acid does not contain any functional groups. [A1] is preferably glycine. x is preferably 1. The presence of an inert amino acid or short chain of inert amino acids such as glycine at position [A1] of formula (I) provides flexibility to the structure. This also helps to minimize racemisation during synthesis.

The group [P]$_{n'}$[Lys]$_n$ is a dentritic structure formed from n lysine groups and n' groups P. The or each lysine is bound to another lysine group via its carboxy terminus. Where the dentritic structure contains only one lysine group, that lysine group is bound via its carboxy terminus to the lysine group adjacent to the spacer.

The or each lysine group is typically also bound to two further groups via each —NH$_2$ group in the lysine structure. The two further groups are selected from further lysine groups and groups P. In this way, a dendritic structure of cascading lysine molecules is typically built up. Preferably, at least 3 lysines are present in the dentritic structure (n=3). Most preferably 7 lysines are present (n=7). More than 7, for example up to 15 (n=15), lysines may be present if desired.

In one embodiment of the invention, no groups P are present (n'=0). In this embodiment the terminal groups of the dentritic structure are lysine groups. This embodiment has the advantage that the lysine groups impart anticoagulant effect to the polymer. Alternatively, one or more groups P are present. Typically, each terminal lysine in the dentritic structure is bound to two P groups (n'=n+1).

The groups P may be the same or different and are selected from heparin, amino acids and peptides. Preferably, each P is the same. Where the group P is a peptide, it typically contains up to 30, for example up to 25, 20 or 16 amino acids. Examples of suitable peptides for use as the group P are blood compatible anticoagulant peptides. Any blood compatible anticoagulant peptide known in the art may be used, but specific examples include RGD (Arg-Gly-Asp), GRGDG (Gly-Arg-Gly-Asp-Gly) and heparin. The KRAD-7 peptide (containing 7 KRAD units, i.e. (Lys-Arg-Ala-Asp)$_7$) can also be used.

Other peptides that can be used as the group P are growth peptides and chemotactic peptides, for example those mentioned below with reference to the chain extenders. Specific examples of growth peptides are those derived from VEGF (vascular endothelial growth factor) or IGF (insulin-like growth factor), including IGF-1 and IGF-2. Such peptides are optionally present in protected form, for example wherein the —NH$_2$ terminus is protected, for example with methyl groups.

Any amino acid or peptide present as the group P may, optionally, be present in its D-form, rather than the normal (and naturally occurring) L-form. In this embodiment, where P is a peptide, each amino acid of the peptide has the D-form. Thus, for example, when P is RGD, each amino acid R, G and D is present in the in the D-form. This embodiment has the advantage that the D-amino acids or peptides are generally more resistant to degradation than the L-amino acids or peptides and copolymers containing segments of formula (I) in which the group P is in the D-form may have a higher patency rate than corresponding copolymers in which the L-form is used. In this embodiment, the order of the amino acids in any peptide is not reversed. Thus, when the peptide is RGD, whether the D- or L-peptide is used, it is still the R amino acid that is connected to the lysine dendrimer.

The Spacer of the segments of formula (I) is a fatty acid, inert peptide or PEG. The structure of the Spacer is not particularly limited. An inert peptide is a series of two or more inert amino acids, wherein an inert amino acid is as defined above with regard to [A1]. A preferred inert amino acid is glycine. Preferred Spacers are fatty acids and PEG. Examples of suitable fatty acids include $C_4$ to $C_{18}$ fatty acids, e.g. butanoic and hexanoic acid.

Varying the length of the Spacer alters the stability of the structure as the point of attachment of the segment to the polymer backbone varies. Increased stability is provided by increasing the length of the Spacer.

The functional part of each pendant group segment may be attached to the polymer backbone via a pendant arm. A pendant arm is thus a group which connects the functional part of a pendant group segment to the backbone of the polyurethane polymer. Typically, the pendant group does not impart functionality to the final polymer.

The pendant arm is typically an aliphatic group. For example, the pendant arm may be a hydrocarbon group which is straight or branched and may contain cyclic moieties. It may be unsaturated or saturated. One or more non adjacent, saturated carbon atoms in the hydrocarbon chain may be replaced with a silicon, oxygen, sulfur or nitrogen atom, preferably a silicon or nitrogen atom. Typically the pendant arm contains from 3 or 4 to 24 carbon atoms, for example from 4 to 18 or from 4 to 10 carbon atoms. Preferably the pendant arm is a saturated aliphatic group. More preferably, the pendant arm is a saturated aliphatic hydrocarbon group, which is straight or branched and may contain cyclic moieties, which contains from 3 or 4 to 24 carbon atoms and which optionally has 1, 2 or 3 heteroatoms selected from Si, N, O and S, preferably Si and N, in the hydrocarbon chain.

The pendant arm typically does not contain ether groups since these can lead to oxidation of the polymer in vivo. Thus, the pendant group segments typically do not contain ether groups.

The pendant arm may be unsubstituted or substituted, typically with from 1 to 6, preferably from 1 to 4 substituents. Substituents may be present on the straight, branched or cyclic parts of the hydrocarbon chain or on a nitrogen or silicon atom present in the chain. Typically the substituents are selected from halogen atoms, $C_1$-$C_4$ alky, $C_1$-$C_4$ alkoxy and $C_1$-$C_4$ alkylthio groups and groups of formula —$NR^1R^2$ wherein $R^1$ and $R^2$ are the same or different and are selected from $C_1$-$C_4$ alkyl groups. Preferred substituents include methyl, ethyl, methoxy, methylthio and dimethylamino groups. Halogen substituents, in particular fluorine, are also preferred substituents. Fluorine substituents may provide improved strength to the polymer as well as anti-inflammatory properties.

The pendant arm may incorporate peptides or polypeptides, for example as a substituent or as a part of the main chain of the pendant arm. Examples of suitable peptides are blood compatible anticoagulant peptides. Any blood compatible anticoagulant peptide known in the art may be used, but specific examples include RGD (Arg-Gly-Asp), lysine and multipeptides of lysine, for example polpypeptides containing up to 10, for example 3 lysine units. The KRAD-7 peptide (containing 7 KRAD units, i.e. (Lys-Arg-Ala-Asp)$_7$) can also be used. Other peptides that can be incorporated into the pendant aim are growth peptides and chemotactic peptides, for example those mentioned below with reference to the chain extenders.

The length of the pendant arm may be varied to control the properties of the final copolymer. For example, the use of a shorter pendant arm renders the functional part of the pendant group physically closer to the copolymer chain. Where the functional part of the pendant group segment is a bulky group such as a silsesquioxane cage or a partial cage, this renders the copolymer harder.

The pendant arm is attached to one or two (or optionally three) neighbouring segments in the copolymer chain, e.g. via urea or urethane groups. The pendant arm may be joined to the neighbouring segments through any part of the pendant arm, including to the straight, branched or cyclic part of the hydrocarbon chain. If a nitrogen atom replaces one of the carbon atoms of the hydrocarbon chain, this nitrogen atom may form a part of a urea or urethane linking group.

The pendant arm may be attached to the neighbouring segments (e.g. via urea/urethane groups) either in a primary or secondary manner. Primary attachments are those wherein the neighbouring segment (e.g. via a urea or urethane group) is attached to a primary carbon atom in the pendant arm and secondary attachments are to a secondary carbon atom in the pendant arm. A more rigid copolymer can be formed if the silsesquioxane, or other pendant group segment, is joined to two neighbouring segments, both via a primary attachment.

The copolymers of the invention may comprise one type of pendant group segment, or they may comprise two or more different types of pendant group segment. For example, the polymer may comprise two or more different silsesquioxane segments. This embodiment is particularly advantageous as the polymer exhibits improved anti-platelet properties. Alternatively, the copolymer may comprise, for example, silsesquioxane segment(s) as well as phosphoryl choline segment(s), and/or di- or tri-fluoromethyl containing segments and/or heparin-like segment(s) and/or segment(s) containing a group of formula (I). Alternative combinations of pendant groups are also possible.

The copolymers of the invention comprise one or more polyol segments. Preferred polyol segments are polycarbonate, polyether, polyester or polybutadiene polyols. Polycarbonate segments are preferred for medical applications since they have a higher biocompatibility due to their decreased rate of degradation in vivo. Polyethers are particularly useful for non-medical applications. Suitable polyol segments are those known in the art for the production of polyurethanes for use as implantable devices, or other devices.

Each polyol segment typically has a molecular weight of from 1000 to 3000 Daltons, preferably from 1500 to 2500 Daltons. Molecular weights in the region of 2000 Daltons are preferred where the copolymer is to be used as an implantable device, although alternative molecular weights can be envisaged where the copolymer is to have a different end use.

Where more than one polyol segment is present in a copolymer of the invention, each such segment is the same or different. Typically, each polyol segment comprises only one type of polymer. Thus, the polymer typically comprises, for example only polycarbonate, or only polyether, segments. The lengths of each of the polyol segments present in a copolymer of the invention are typically different from one another.

Typically, the copolymers of the invention contain more polyol segments than pendant group segments. Thus, the ratio of pendant group segment: polyol segment is less than 1:1. Preferred copolymers have a ratio of pendant group segment: polyol segment of 1:10 or less, more preferably 1:25 or less, in particular a ratio of 1:50 or less.

Further, the copolymers of the invention contain may more polyol segments than pendant siloxane segments. Thus, the ratio of pendant siloxane segment: polyol segment is less than 1:1. Preferred copolymers have a ratio of pendant siloxane segment: polyol segment of 1:10 or less, more preferably 1:25 or less, in particular a ratio of 1:50 or less.

The polymers of the invention include, for example, polyurethanes, PTFE, polyethylene terephthalate, polyamides, polypropylene and nylon. The types of polymers which can be made are not particularly limited but are typically polymers appropriate for manufacture of implantable devices. Polyurethanes are preferred, at least in part due to their good toughness and mechanical strength.

Where the polymers are polyurethanes, each segment of the copolymer of the invention is linked to one or more neighbouring segments by urea or urethane linkages, which typically have the formula

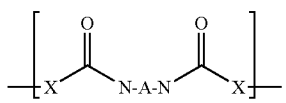

wherein each X is the same or different and is a nitrogen or oxygen atom and each A is the same or different and is an aromatic or aliphatic moiety. Each N is bound to one further group in addition to the depicted -A- and —COX— groups. This further group is typically a hydrogen atom.

The group A is typically derived from a diisocyanate compound. Thus, preferred groups A are those which form readily available diisocyanate compounds when the groups —NC(O)—X— in the above formula are each replaced with an isocyanate group.

Typically, when A is an aliphatic moiety it is an unsubstituted, straight or branched $C_1$-$C_{12}$, preferably $C_3$-$C_9$, alkylene moiety, a $C_3$-$C_8$ cycloalkylene moiety or a group of formula —($C_3$-$C_8$ cycloalkyl)-($C_1$-$C_2$ alkylene)-($C_3$-$C_8$ cycloalkyl)-. Preferred $C_3$-$C_8$ cycloalkylene moieties include cyclohexylene and cyclopentylene. Preferred groups of formula —($C_3$-$C_8$ cycloalkyl)-($C_1$-$C_2$ alkylene)-($C_3$-$C_8$ cycloalkyl)- include methylene-biscyclopentylene and methylene-biscyclohexylene. Examples of suitable aliphatic groups A include butylene, 2-methylpentylene, hexylene, octylene and methylene-biscyclohexylene moieties, in particular methylene-biscyclohexylene.

Typically, when A is an aromatic moiety, it is a phenylene, naphthylene or methylene-bisphenylene group, each of which is unsubstituted or substituted with 1, 2 or 3 substituents selected from halogen atoms, $C_1$-$C_4$ alkyl, $C_1$-$C_4$ alkoxy and $C_1$-$C_4$ alkylthio groups and groups of formula —$NR^1R^2$ wherein $R^1$ and $R^2$ are the same or different and are selected from hydrogen atoms and $C_1$-$C_4$ alkyl groups. Preferred substituents include methyl, ethyl, methoxy, methylthio, amino and dimethylamino groups, in particular methyl. A may be linked to the groups —N—C(O)—X— either via the aromatic ring or via a substituent.

Preferably, when A is an aromatic moiety it is a phenylene, methylphenylene, dimethylphenylene, naphthylene, methylene-bisphenylene, 1,3-bis-(1-methylethyl)benzene or dimethoxybenzidinyl moiety, in particular a methylphenylene, 1,3-bis-(1-methylethyl)benzene or methylene-bisphenylene moiety.

Preferably A is an aromatic moiety, since the resulting copolymer is typically more resistant to oxidation and thus biodegradation than a copolymer containing aliphatic moieties at the corresponding positions. A particularly preferred group A is methylene-bisphenylene.

The copolymers of the invention typically comprise one or more chain extender segments (c), each of said chain extender segments being liked to one or more further segments, which may be the same or different, via urethane or urea linkages, as described above. Thus, the chain extender segment(s) may be present either within the copolymer structure or at the end of the copolymer chain, depending on whether the chain extender segment in question is linked to either one or two further segments.

The chain extender segment(s) may be any commonly known chain extender used in the production of polyurethane groups. Thus, for example, the chain extenders may be simple alkylene groups such as ethylene groups. However, more complex chain extenders may also be used such as amino acids, peptides and polypeptides. The preferred chain extenders for use in the present invention are amino acids, peptides, polypeptides and $C_1$-$C_6$ aliphatic moieties.

The use of amino acids, peptides and polypeptides, in particular polypeptides, as chain extender segments enables functionality to be introduced into the copolymer chain. For example, the polypeptide may be RGD (Arg-Gly-Asp), a polypeptide that enhances non-thrombogenicity. Introducing such a polypeptide into the copolymer chain provides a final polyurethane having inherently increased biocompatibility. This therefore removes the need to attach groups such as RGD to the polymer after its formation. Thus, a non-thrombogenic polymer can be produced without altering the mechanical properties of the copolymer.

Polypeptides that can be introduced into the copolymers of the invention in this way include anticoagulant peptides, growth peptides or chemotactic peptides, especially heparin and/or RDG (Arg-Gly-Asp). Examples of anticoagulant peptides which can be used include any blood compatible anticoagulant peptide known in the art. Examples of suitable anticoagulant peptides include RGD, lysine and multipeptides of lysine, for example polpypeptides containing up to 10, for example 3 lysine units. The KRAD-7 peptide (containing 7 KRAD units) can also be used.

The presence of anticoagulant peptides such as those mentioned above in the copolymers of the invention has the advantage that, when a prosthesis formed from such a polymer is inserted into a patient, the anticoagulant effect is immediate. This is in contrast with the lining of the polymer with seed cells, since it takes some time for a full endothelial layer to form from the relatively few endothelial cells that adhere to the polymer surface during seeding.

Examples of suitable growth peptides for use as chain extender segments include any peptides known in the art to encourage the growth of the endothelial layer. Typical growth peptides are Arg-Gly-Asp, fibronectin fragments 1371-1382 and 1377-1388, for example as described by Mohri,H et al (Peptides.1995, 16: page 263), fibronectin adhesion promoting peptide, for example as described by Woods, A., et. al. (Mol. Biol. Cell, 1993; 4: page 605), Gly-Arg-Gly-Asp, for example as described by Haverstick, DM. et. al. (Blood; 1985; 66: page 946).

Examples of suitable chemotactic peptides are those which attract endothelial cells to the surface to which they are attached, in the case of vascular grafts, the lumen of the graft. N-Formyl peptides are suitable for these purposes as they secrete chemoattractants which direct the migration of cells to the chemoattractant source. Fibronectin fragments and related peptides can also be used. These proteins promote adhesion of endothelial cells to the graft lumen and also to other cells. They also help to stabilise clot formation. Further details regarding chemotactic proteins can be found in Freer R. J., et al. 1979; Peptides, structure and biological function; Proceedings of the sixth American peptide symposium; Gross,E and Meienhofer, M., eds.:749 and Procter, R A; Rev. Infect. Dis. 1987; 9: page 317.

NO releasing agents may also be incorporated into the polymer, for example as cross-linking segments, as a part of the pendant arm or as a group P in the segments containing a group of formula (I) (Zhang H et al, Biomaterials 2002 Mar; 23(6):1485-94, incorporated herein by reference). Examples of NO releasing agents include the group of non-linear optic materials disperse red, disperse yellow and disperse orange. Particular examples are disperse red 1 and 19, disperse yellow 3 and 7 and disperse orange 13.

The copolymer of the invention may comprise one or more different types of chain extender segment. For example, the copolymer may contain one or more chain extenders which are $C_1$-$C_6$ aliphatic moieties, preferably ethylene, and one or more chain extender segment(s) which are amino acids, peptides or polypeptides, preferably polypeptides, such as those described above.

Preferred copolymers of the invention have a value of tensile stress at 100% elongation of at least 7, preferably at least 8 N/mm² (measured according to ASTM D1708 on a Shimadzu machine at a displacement rate of 10 mm/min). At 300% elongation the tensile stress is preferably at least 15, preferably at least 16, more preferably at least 17 N/mm² (also measured according to ASTM D1708 on a Shimadzu machine at a displacement rate of 10 mm/min). The copolymers preferably have a tear strength of at least 90, preferably at least 93 kN/m (measured according to ASTM D624 using a die "C" specimen geometry and conducted on a Shimadzu machine at a rate of 500 mm/min).

The copolymers of the invention typically comprise units derived from
(a) one or more pendant group components selected from
  (i) siloxane components;
  (ii) components containing phosphoryl choline or a derivative or analogue thereof;
  (iii) components containing a di- or trifluoromethyl group;
  (iv) heparin-like components containing a group of formula (XII)

D-N=N—Ar—$SO_3^-$ (XII)

wherein D is an aliphatic or aromatic group and Ar—$SO_3^-$ comprises one or more linked aryl and/or heteroaryl groups, at least one of the aryl and/or heteroaryl groups having an $SO_3^-$ substituent; and
  (v) components containing a group of formula (I)

$[P]_{n'}$-$[Lys]_n$-[Spacer]-Lys-[A1]$_x$ (I)

wherein:
  [A1] is an inert amino acid;
  x is 0, 1, 2 or 3;
  [Spacer] is a fatty acid, amino acid, peptide or PEG;
  $[P]_{n'}$-$[Lys]_n$ is a dendritic structure formed from n lysine groups and terminating in n' groups P;
  n is an integer of from 1 to 15;
  n' is zero or an integer of up to 16; and
  each P is the same or different and is heparin, an amino acid or a peptide;
(b) a polyol;
(c) an aromatic compound having two or more isocyanate groups; and optionally
(d) one or more chain extenders selected from amino acids, peptides, polypeptides and $C_1$-$C_6$ aliphatic groups, each of which has at least one substituent selected from primary and secondary amine, hydroxyl and carboxylic acid groups.

In a preferred embodiment, the copolymers of the invention comprise comprise units derived from
(a) a siloxane component;
(b) a polyol;
(c) an aromatic compound having two or more isocyanate groups; and optionally
(d) one or more chain extenders selected from amino acids, peptides, polypeptides and $C_1$-$C_6$ aliphatic groups, each of which has at least one substituent selected from primary amine, hydroxyl and carboxylic acid groups.

A pendant group (or siloxane) component is a pendant group (or siloxane) segment as defined above having primary or secondary amine, hydroxyl or carboxylic acid groups at the locations in which the pendant group (or siloxane) segment is attached to the urea or urethane groups in the copolymer backbone.

The copolymers of the invention may be produced by standard polymerisation techniques. The pendant group segments may be incorporated by including in the polymerisation mixture one or more pendant group segments linked to polymerisable groups. The production of the copolymers of the invention will be described in more detail below with reference to the production of polyurethane polymers. The skilled person would be able to make the necessary alterations to this process in order to produce different types of polymer.

The copolymers of the invention comprising linear siloxanes which are attached directly to the polyurethane copolymer can be produced by reacting a pre-prepared polyol polyurethane with a strong base such as NaH. This forms an anion on a nitrogen atom of the polyurethane group as depicted in Scheme I below:

Scheme I

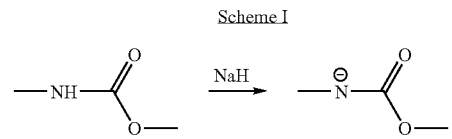

The anion produced acts as a typical nucleophile and can be reacted with a siloxane to attach a silicon atom of the siloxane to the nitrogen atom. For example, cyclic siloxanes such as hexamethylcyclotrisiloxane, can be reacted with the anion in a ring-opening reaction as depicted in Scheme II.

Scheme II

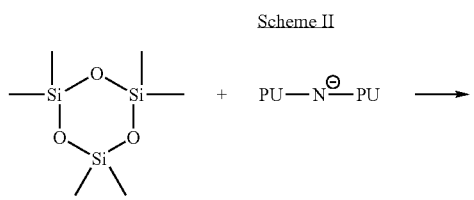

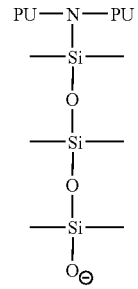

wherein PU is a polyol polyurethane.

A chain terminator is also typically added to the reaction mixture, for example $(CH_3)_3Cl$.

Reaction can also be carried out with linear siloxane reagents. Such linear siloxane reagents are typically those of formula

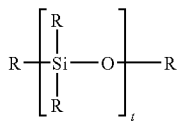

wherein R is as defined above and t is an integer corresponding to the number of siloxane units in the siloxane polymer. t is typically 2 or more, for example from 2 to 50, or from 2 to 30. An example of a linear siloxane reagent is $(CH_3)_3Si—O—Si(CH_3)_3$.

Cyclic and linear siloxane reagents are typically available commercially or can be produced using well known techniques.

An alternative process for producing the copolymers of the invention is a process comprising polymerising, in any order,
(i) one or more pendant group segments, the or each segment being bonded to at least one group selected from primary or secondary amine, hydroxyl and carboxylic acid groups;
(ii) a polyol;
(iii) an aromatic compound having two or more isocyanate groups; and optionally
(iv) one or more chain extenders selected from amino acids, peptides, polypeptides and $C_1$-$C_6$ aliphatic groups, each of which has at least one substituent selected from primary or secondary amine, hydroxyl and carboxylic acid groups.

The components (i) and (iv) each comprise at least one polymerisable group selected from primary or secondary amine, hydroxyl and carboxylic acid groups. Preferred polymerisable groups are primary amine, hydroxyl and carboxylic acid groups, in particular primary amine and hydroxyl groups.

Where the pendant group segment is intended to be present at the end of the copolymer chain, the component (i) typically has only one group selected from primary or secondary amine, hydroxyl and carboxylic acid groups. Where the pendant group segment is intended to be present other than at the end of the copolymer chain, the component (i) typically has at least two groups selected from primary or secondary amine, hydroxyl and carboxylic acid groups.

Similarly, where the chain extender segments are intended to be at the end of the copolymer chain, only one substituent selected from primary or secondary amine, hydroxyl and carboxylic acid groups is present on the chain extender component (iv). Otherwise, where these segments are intended to be other than at the end of the copolymer chain, at least two substituents selected from primary or secondary amine, hydroxyl and carboxylic acid groups are present.

If it is desired to introduce cross-linking into the copolymer chain, the component (i) may have at least three groups selected from primary or secondary amine, hydroxyl and carboxylic acid groups. Similarly, the polyol and/or chain extender components (ii) and (iv) may bear three or more polymerisable groups (hydroxyl, primary or secondary amine or carboxylic acid groups). Cross-linking can also be introduced by using an isocyanate component (iii) having three or more isocyanate groups.

In the component(s) (i), the primary or secondary amine, hydroxyl or carboxylic acid group(s) are present on the pendant group segment at the position(s) in which the pendant group segment is to be attached to the urea or urethane linkage(s) in the final copolymer.

Where the copolymer to be produced comprises one or more siloxane segments, the component (i) above comprises a siloxane segment having at least one group selected from primary or secondary amine, hydroxyl and carboxylic acid groups. Preferred siloxane components (i) are those of formula S—Y'$L_x$, for example S—Y'$L_2$, wherein S is as defined above, Y' is an aliphatic group having at least one substituent L, each L is the same or different and is selected from primary or secondary amine, hydroxyl and carboxylic acid groups, and x is at least one, for example one, two or three.

Where the siloxane segment is intended to be present at the end of the copolymer chain, group Y' of component (i) has one substituent L (x=1). Where the siloxane segment is intended to be present other than at the end of the copolymer chain, group Y' of component (i) has at least two substituents L (x≧2). If it is desired to introduce cross-linking into the copolymer chain, the group Y' of the silsesquioxane component (i) may bear three or more substituents L (x≧3).

The group S of the siloxane component (i) is defined above. Thus, the group S may be a linear siloxane or a silsesquioxane cage or partial cage. Further, the group Y' is typically a group Y as defined above which is bonded to two substituents L.

Where the copolymer to be produced comprises one or more segments containing phosphoryl choline or derivatives or analogues thereof, the component (i) above comprises a segment containing phosphoryl choline or a derivative or analogue thereof, and having at least one, for example at least two or at least three, groups selected from primary or secondary amine, hydroxyl and carboxylic acid groups.

Where the copolymer to be produced comprises one or more segments containing a di- or trifluoromethyl group, the component (i) above comprises a segment containing a di- or trifluoromethyl group, and having at least one, for example at least two or at least three, groups selected from primary or secondary amine, hydroxyl and carboxylic acid groups.

Where the copolymer to be produced comprises one or more segments containing a heparin-like group of formula (XII), the component (i) above comprises a segment containing a group or formula (XII), and having at least one, for example at least two or at least three, groups selected from primary or secondary amine, hydroxyl and carboxylic acid groups.

Where the copolymer to be produced comprises one or more segments containing a group of formula (I), the component (i) above comprises a segment containing a group of formula (I), and having at least one, for example at least two or at least three, groups selected from primary or secondary amine, hydroxyl and carboxylic acid groups. The groups selected from primary or secondary amine, hydroxyl and carboxylic acid groups are typically the free —$NH_2$ groups present on the lysine groups either side of the Spacer.

During polymerisation, the amino acid or peptide groups P are optionally protected. For example, protecting groups may be applied-to the free $NH_2$ terminus of the amino acid or peptide. Any suitable protection strategies may be used.

A polyol component (ii) is typically a polyol segment as described above, and has at least two hydroxyl groups. Alternatively, the polyol component (ii) comprises a polyol chain linked to one or more further segments, each of which may be the same or different. Typically each of said segments are linked via urea or urethane groups.

A chain extender component (iv) is typically a chain extender segment as described above wherein one or both ends of the chain extender segment are bonded to hydroxyl, primary amine or carboxylic acid groups. Alternatively, the chain extender component (iv) comprises a chain extender segment linked to one or more further segments, each of which may be the same or different. Typically each of said segments are linked via urea or urethane groups.

The above definitions of components (i), (ii) and (iv) encompass compounds having two adjacent hydroxyl groups. It is noted that such adjacent hydroxyl groups may instead form an epoxide group. Such components having an epoxide group as a substituent are therefore also encompassed within the scope of the present invention. Prior to reaction, the epoxide group should be opened to provide the corresponding diol.

The isocyanate component (iii) is typically a moiety A as described above which is bonded to two or more isocyanate groups. Typically, the isocyanate component (iii) has two isocyanate groups, i.e. it is a diisocyanate. Suitable diisocyanate compounds for use as the component (iii) are commercially available diisocyanates including those commonly used in the manufacture of polyurethanes.

The copolymers of the invention can be synthesised by forming a melted mixture of polyol component (ii) and component (i) and subsequently adding the isocyanate component (iii). This type of method is typically used where the component (i) is a siloxane. Polymerisation is typically carried out at a temperature of from 50 to 150° C. for a period of approximately 1 to 3 hours.

Alternatively, a solution polymerisation may be carried out, in which the components (i), (ii) and (iii) are dissolved or suspended in an organic solvent, for example an aprotic solvent such as dimethylacetamide (DMAC) or THF. Where the component (i) comprises a segment containing phosphoryl choline or a derivative thereof, the solvent may be DMSO.

If a chain extender component is to be used, this is typically added after the above step has been completed. For example, the prepolymer of polyol with siloxane may be dissolved in a suitable aprotic solvent such as dimethylacetamide (DMAC) and a solution of the chain extender component, typically also dissolved in the same solvent, added to the resulting solution. The chain extender is then incorporated into the copolymer chain by reaction with remaining isocyanate component. An alcohol such as butanol is typically added to terminate the reaction.

Alternative orders of addition of the components may also be used if desired. For example, the components (ii) and (iii) may be mixed initially to form a prepolymer of polyol and the component (i), e.g. the siloxane, and optionally chain extender components added subsequently. Where more than one component (i) is used, the components may be added to the polymerisation mixture either substantially simultaneously or separately. For example, a siloxane component could be polymerised with the polyol and isocyanate, and a component of formula (I) added at a later stage, for example at the same time as a chain extender component.

Where the component (i) comprises a segment containing phosphoryl choline or a derivative thereof, the phosphoryl choline containing component is typically added after an initial prepolymer of polyol and isocyanate, and optionally further components (i), has been formed. This order of addition is particularly preferred where the phosphoryl choline derivative is of formula (V) wherein B is an aliphatic group such as an alkylene group. This is because such components can be difficult to work with. One advantage of using a group B comprising a heteroaryl group, in particular a group B of formula (VI) as set out above, is that the component containing phosphoryl choline becomes easier to handle.

A large number of siloxane components (i) are commercially available. Standard synthetic techniques can also be used to produce alternative siloxane components, for example by adapting commercially available siloxane components.

Examples of silsesquioxane components which can be used as starting materials in producing the copolymers of the invention include
1,3,5,7,9,11-Octaisobutyltetracyclo[7.3.3.1(5,11)]octasiloxane-endo-3,7,diol, 1,3,5,7,9,11,13,15-octakis(dimethylsilyloxy)pentacyclo[9.5.1.1$^{3,9}$.1$^{5,15}$.1$^{7,13}$]-octasiloxane,
3-(3,5,7,9,11,13,15-heptacyclopentylpentacyclo[9.5.1.1$^{3,}$ $_9$.1$^{5,15}$.1$^{7,13}$]octasiloxan-1-yl)propyl methacrylate,
1,3,5,7,9,11,13-Heptacyclopentyl-15-glycidylpentacyclo [9.5.1.1$^{3,9}$.1$^{5,15}$.1$^{7,13}$]-octasiloxane,
3,5,7,9,11,13,15-Heptacyclopentylpentacyclo[9.5.1.1$^{3,9}$.1$^{5,}$ $_{15}$.1$^{7,13}$]-octasiloxan-1-ol, (Glycidoxypropyldimethylsilyloxy)heptacyclopentylpentacyclooctasiloxane,
1-[2-(3,4-Epoxycyclohexyl)ethyl]-3,5,7,9,11,13,15-isobutylpentacyclo-[9.5.1.1(3,9).1(5,15).1(7,13)]octasiloxane (epoxycyclohexylisobutyl-POSS), Epoxycyclohexylethyl-POSS,
1-(2-trans-Cyclohexanediol)ethyl-3,5,7,9,11,13,15-isobutylpentacyclo-[9.5.1.1(3,9).1(5,15).1(7,13)]octasiloxane (trans-cyclohexanediolisobutyl-POSS)
1-(4-Vinylphenyl)-3,5,7,9,11,13,15-heptacyclopentylpentacyclo-[9.5.1.1$^{3,9}$.1$^{5,15}$.1$^{7,13}$]octasiloxane,
1-Vinyl-3,5,7,11,13,15-isobutylpentacyclo[9.5.1.1(3,9).1(5, 15).1(7,13)]-octasiloxane,
1-(2,3-Propanediol)propoxy-3,5,7,9,11,13,15-isobutylpentacyclo-[9.5.1.1(3,9).1(5,15).1(7,13)]octasiloxane,
1-[3-(2-Aminoethyl)amino]propyl-3,5,7,9,11,13,15-isobutyl pentacyclo-[9.5.1.1(3,9).1(5,15).1(7,13)]octasiloxane,
Dodecaphenyl-POSS Further examples also appear in FIGS. 1 and 2. Some of these components must be pre-functionalised in order to provide suitable polymerisable groups on the silsesquioxane component. For example, compounds containing an epoxide ring are typically ring-opened to provide a diol which can take part in the polymerisation reaction. Such pre-functionalisation reactions are well known to the skilled person.

Examples of the compounds which can be used without pre-functionalisation, or following simple epoxide ring-opening, include
1,3,5,7,9,11-Octaisobutyltetracyclo[7.3.3.1(5,11)]octasiloxane-endo-3,7,diol, 3-(3,5,7,9,11,13,15-heptacyclopentyl-pentacyclo[9.5.1.1$^{3,9}$.1$^{5,15}$.1$^{7,13}$]octasiloxan-1-yl)propyl methacrylate,
1,3,5,7,9,11,13-Heptacyclopentyl-15-glycidylpentacyclo [9.5.1.1$^{3,9}$.1$^{5,15}$.1$^{7,13}$]-octasiloxane,
3,5,7,9,11,13,15-Heptacyclopentylpentacyclo[9.5.1.1$^{3,9}$.1$^{5,}$ $_{15}$.1$^{7,13}$]-octasiloxan-1-ol, (Glycidoxypropyldimethylsilyloxy)heptacyclopentylpentacyclooctasiloxane,
1-[2-(3,4-Epoxycyclohexyl)ethyl]-3,5,7,9,11,13,15-isobutylpentacyclo-[9.5.1.1(3,9).1(5,15).1(7,13)]octasiloxane (epoxycyclohexylisobutyl-POSS),
Epoxycyclohexylethyl-POSS,
1-(2-trans-Cyclohexanediol)ethyl-3,5,7,9,11,13,15-isobutylpentacyclo-[9.5.1.1(3,9).1(5,15).1(7,13)]octasiloxane (trans-cyclohexanediolisobutyl-POSS)1-(2,3-Propanediol)propoxy-3,5,7,9,11,13,15-isobutylpentacyclo-[9.5.1.1(3,9).1(5,15).1(7,13)]octasiloxane,
1-[3-(2-Aminoethyl)amino]propyl-3,5,7,9,11,13,15-isobutyl pentacyclo-[9.5.1.1(3,9).1(5,15).1(7,13)]octasiloxane.

Examples of partial-cage silsesquioxane components which can be used as starting materials in producing the copolymers of the invention include
1,3,5,7,9,11,14-Heptacyclopentyltricyclo[7.3.3.1$^{5,11}$]heptasiloxane-endo-3,7,14-triol, 1,3,5,7,9,11,14-Heptacyclohexyltricyclo[7.3.3.1$^{5,11}$]heptasiloxane-3,7,14-triol,
(−)-3',5'-O-(1,1,3,3-Tetraisopropyl-1,3-disiloxanediyl)adenosine,
(+)-3',5'-O-(1,1,3,3-Tetraisopropyl-1,3-disiloxanediyl)cytidine.

Figure 4A:
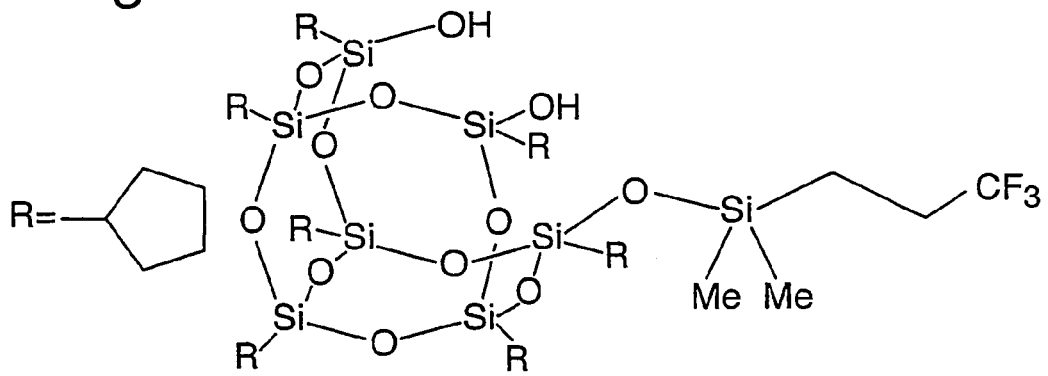
FIG. 4 depicts examples of compounds containing a partial silsesquioxane cage as well as a trifluoromethyl group.
Figure 4B:
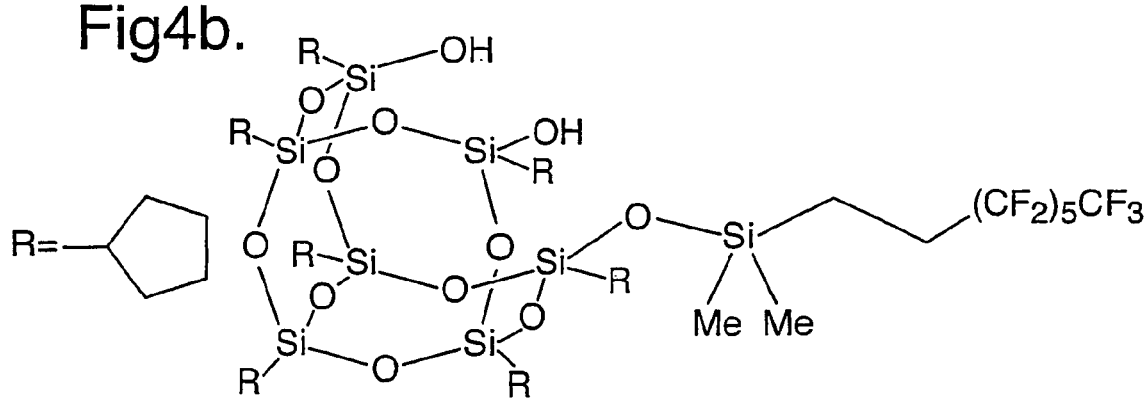

Further examples are depicted in FIGS. 3 and 4.

A variety of components containing phosphoryl choline and derivatives and analogues thereof are also commercially available or can be produced using standard synthetic techniques. Phosphoryl choline derivatives of formula (V) wherein B is an aliphatic group such as an alkylene group can be prepared in accordance with Scheme (III) below.

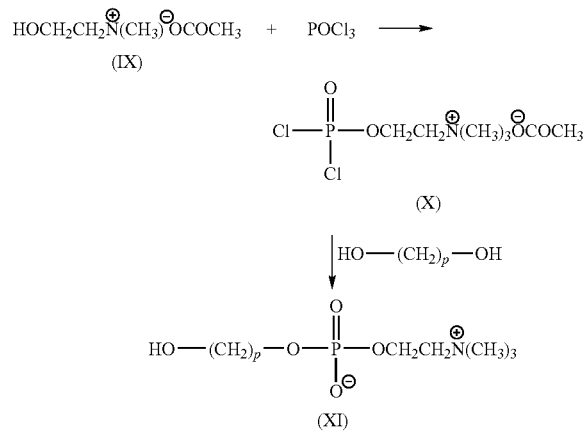

This scheme depicts the functionalisation of phosphoryl choline by formation of the choline acetate dichlorophosphate (X). The compound (X) is here reacted with a diol to form a phosphoryl choline derivative (XI), but reaction with polymers or other compounds containing free hydroxyl, amine or carboxylic acid groups is also envisaged.

Commercially available examples of components containing phosphoryl choline and derivatives and analogues thereof include
2'-Deoxyadenosine-5'-monophosphoric acid,
2'-Deoxycytidine-5'-monophosphoric acid,
2'-Deoxyguanosine 5'-monophosphate,
Cytidine 5'-triphosphate
Adenosine 2',3'-cyclic monophosphate
(−)-Adenosine 3',5'-cyclic monophosphate
Adenosine 5'-triphosphate
Thymolphthalein monophosphoric acid Components containing a di- or trifluoromethyl group are commercially available or can be produced by standard synthetic techniques. For example, trifluoromethyl functional groups may be added to a compound by replacement of a leaving group.

Components containing the heparin-like groups of formula (XII) are commercially available or can be produced by standard synthetic techniques. Commercially available examples of components containing heparin-like groups include Acid Yellow compounds and other similar dyes.

Components of formula (I) can be produced by standard solid phase methods, for example on a Rink Acid resin (solid phase peptide synthesis H. Rink (1978) Tetrahedron Lett., 28, 3787). The dentritic structure of the components of formula (I) has previously been described in the context of anti-body production (J. P. Tam, Proc. Natl. Sci. USA, 1988, 85, 5409).

The polymers of the invention can, if desired, be lined with cells in order to increase their biocompatibility. The cells which can be used in the present invention include endothelial cells and microvascular cells, preferably endothelial cells. Examples of suitable cells include animal cells, such as animal endothelial cells, or cells which have been harvested from the human vein, typically the saphenous vein or the umbilical vein or from human adipose tissue. Cells are harvested using standard techniques such as those described by Jaffe et al (J. Clin. Invest. 1973; 52; 2745-56). Seeding such cells on the inside surface of a vascular graft is known to encourage the growth of the fall endothelium. This provides a natural defence against particles adhering to the surface of the graft and increases the patency rate. Typically the cells used are derived from the patient's own tissue to avoid rejection.

The process of lining the polymer with cells may be carried out by any technique known in the art. The cells are typically cultivated by any standard cultivation technique such as that described by Zilla et al (J. Vasc. Surg. 1990; 12: pages 180-9). The cells are suspended in a medium which is typically a tissue culture medium. The concentration of cells in the tissue culture medium is preferably from 1 to $50\times10^5$ cells/cm$^2$, preferably from 2 to $24\times10^5$ cells/cm$^2$, more preferably from 2 to $16\times10^5$ cells/cm$^2$.

The medium comprising the cells suspended therein, is then contacted with the copolymer of the invention. Typically, the medium is either inserted into a chamber containing the copolymer and incubated for a period of 0.1 to 10 hours, preferably 0.5 to 6 hours, or the medium is pumped over the copolymer for a period of 0.05 to 10 hours, preferably 0.5 to 6 hours. When the copolymer is in a tubular shape whilst lining is carried out, it may be rotated during incubation or pumping in order to obtain a more even lining of the polymer. The incubation or pumping-procedure may be repeated one or more times to improve the seeding efficiency of the cells. The process is preferably carried out at a temperature of about 37° C.

In order to enhance the adhesion of cells to the copolymer, electrostatic charges may be applied to the copolymer or 0.5 Tesla Helmholz coils may be used, for example before or during the incubation or pumping process.

The copolymers of the invention have a variety of different uses. The copolymers are principally envisaged for use as implantable devices. However, alternative uses maybe made of the copolymers, for instance the copolymers may be used as screens, contact lenses or ocular implants due to their good transparency and lack of discolouration.

Examples of non-medical uses for the polymers of the invention include the use of polyether based polyurethanes as paints. Segments of formula (I) in which the amino acid or peptide P is, for example, an anti-mollusc peptide, can be included in the copolymer which is added to the paint. Such a paint is useful in the protection of a ship's hull as it imparts resistance to molluscs. This has the advantage that the hull requires less frequent cleaning and the ship may move with less drag.

The copolymers are typically processed into moulded articles using standard polymer processing techniques such as extrusion or moulding. Where implantable devices are required, these can be produced, for example, using the technique described by Edwards, A., et al (J. Biomat. App. 1995; 10: pages 171-187). The lining of the copolymer with cells is typically carried out after the polymer has been processed into its desired shape.

Typically, the copolymers of the invention are used to form prostheses, or implantable devices, including vascular grafts, heart valves, stents, including urological stents, conduits for use in surgery to correct nerve damage and orthopaedic joint replacements. Preferred implantable devices are vascular grafts.

The copolymers of the invention may also be envisaged for use in surgical devices other than prostheses. Examples include catheters, plastic tubing through which blood is passed during by-pass operations and tubes used for injecting labelling substances such as In for use in X-ray diagnosis techniques.

The copolymers of the present invention, when in the form of an implantable device, may be used in the treatment of a human or animal subject in need of the replacement of a body part, said method comprising replacing said body part with an implantable device of the invention. Said method may be carried out using standard techniques known in the art of prosthetic surgery. For example, where the implantable device is a vascular graft, the graft may be anastomosed to the natural blood vessel in an end-to-end, end-to-side, or side-to-side manner. The anastomosis is typically carried out using sutures. Alternative methods such as the use of clips or laser techniques are also possible. An advantage of these latter techniques is that they help to retain some of the compliant nature of the graft at the anastomoses.

EXAMPLES

The present invention is further illustrated with reference to the following Examples.

Example 1

A mixture of polycarbonate polyol (2000 MW) (36 g) and silsesquioxane 1 (see FIG. 1 and below) (1 g) were placed in a round bottomed flask equipped with a stirrer, thermometer, stoppers and outlet valve. The mixture was dehydrated by heating under vacuum (1 mm Hg) at 90° C.-110° C. with stirring. This step of the procedure ensures that the silsesquioxane is mixed into the polyol.

After 2 hours the temperature was allowed to fall to 70° C. The system was flushed with dry nitrogen. The top was removed and 4,4'-methylene bisdiphenyl diisocyanate (MDI) was added in one go. The flask top was replaced and the system flushed with dry nitrogen. The temperature was maintained between 75° C. and 85° C. by gentle heating for 2 hours. Dimethylacetamide (DMAC) was added to the system and, on complete dissolution of the reaction mixture in the DMAC, the flask was allowed to cool to room temperature.

The thus formed prepolymer was then chain extended with ethylene diamine using diethylamine as a reaction moderator. The amines were added in DMAC slowly from a dropping funnel. On reaching a viscosity of approximately 30,000 cps, butanol in DMAC was added to stop any further reaction.

Example 1a

Example 1 was repeated using 2,4-methylene bisdiphenyl diisocyanate (MDI).

Examples 2 to 6 and 2a to 6a

Examples 1 and 1a were repeated using silsesquioxanes 2 to 6 as depicted in FIG. 1.

Example 7

A linear siloxane was introduced as a side chain of a polyurethane polycarbonate polymer. A freshly prepared solution of a polycarbonate polyurethane in THF (100 g, 10%), which has been prepared with anhydrous reagents, is place in a 3-necked reaction flask equipped with a stirrer, drying tube and nitrogen purge. The reaction mixture is cooled in an ice water bath to 0-5° C. and sodium hydride (0.5 g) added to the polymer solution. The polymer solution is stirred for one hour to allow formation of anions on the polyurethane groups.

A solution of hexamethylcyclotrisiloxane (4.6 g) and hexamethyldisiloxane (0.05 g) is prepared in anhydrous THF (50 g). This mixture is then added to the reaction mixture and the reaction allowed to proceed for two hours, to form the desired product. Anhydrous conditions should be maintained throughout the reaction and the mixture should be blanketed with dry nitrogen.

Example 8

Stability of Copolymers

Two copolymers were studied for their stability in DMAC. Sample 1 was a control material which was a standard polycarbonate polyurea/urethane. Sample 2 was a copolymer produced according to Example 4 above. Both samples were added to DMAC. Sample 1 was observed to swell and the edges of the material blurred before the sample finally dissolved. Sample 2 maintained its original structure, showed much less swelling and took a longer time to dissolve.

Example 9

The tensile stress and tear strength of (a) the copolymer of Example 4 and (b) a poly(carbonate-urea) urethane formed from a 2000 MW polyol, 4,4'-MDI, ethylenediamine and diethylamine were measured.

The tensile properties of the two polymers were assessed according to ASTM D1708. Tests were conducted on a Shimadzu B1444 testing machine at a displacement rate of 10 mm/min. The tensile stress was recorded at 100% elongation and 300% elongation.

The tear strength was measured according to ASTM D624, using the die "C" specimen geometry. Testing was conducted on a Shimadzu B444 test machine at a rate of 500 mm/min.

The specimens for both tests were cut from the polymer sheets using a template and a scalpel, rather than using a cutting die. A minimum of five samples of each polymer were tested by each test method. For each test, samples were taken from two different sheets of polymers. All tests were performed at room temperature (21° C.).

A summary of the test results is given in Table I. The values quoted are the mean of a minimum of five results and are accompanied by the standard deviation of the results.

TABLE I

|  | New Polymer (POS) | Control Polymer (PU) |
|---|---|---|
| Tensile stress at 100% elongation (N/mm$^2$) | 8.8 +/− 0.29 | 5.8 +/− 1.24 |
| Tensile stress at 300% elongation (N/mm$^2$) | 17.9 +/− 0.52 | 13.1 +/− 3.10 |
| Tear strength (kN/m) | 95 +/− 6.52 | 88 +/− 21.68 |

Example 9a

Figure 5A:
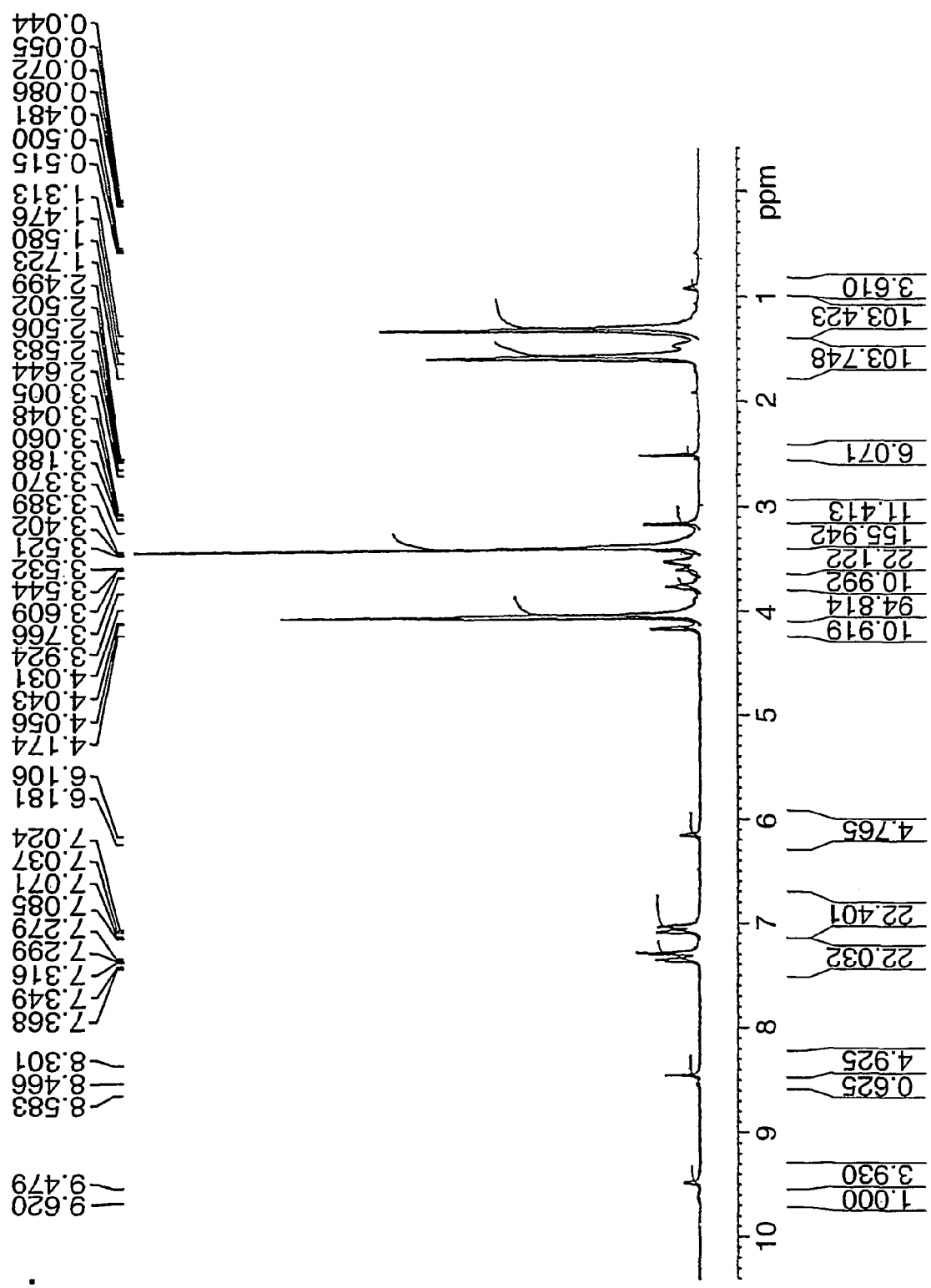
FIG. 5a and 5b depict $^1$H and $^{13}$C NMR spectra respectively for a copolymer of the invention.
Figure 5B:
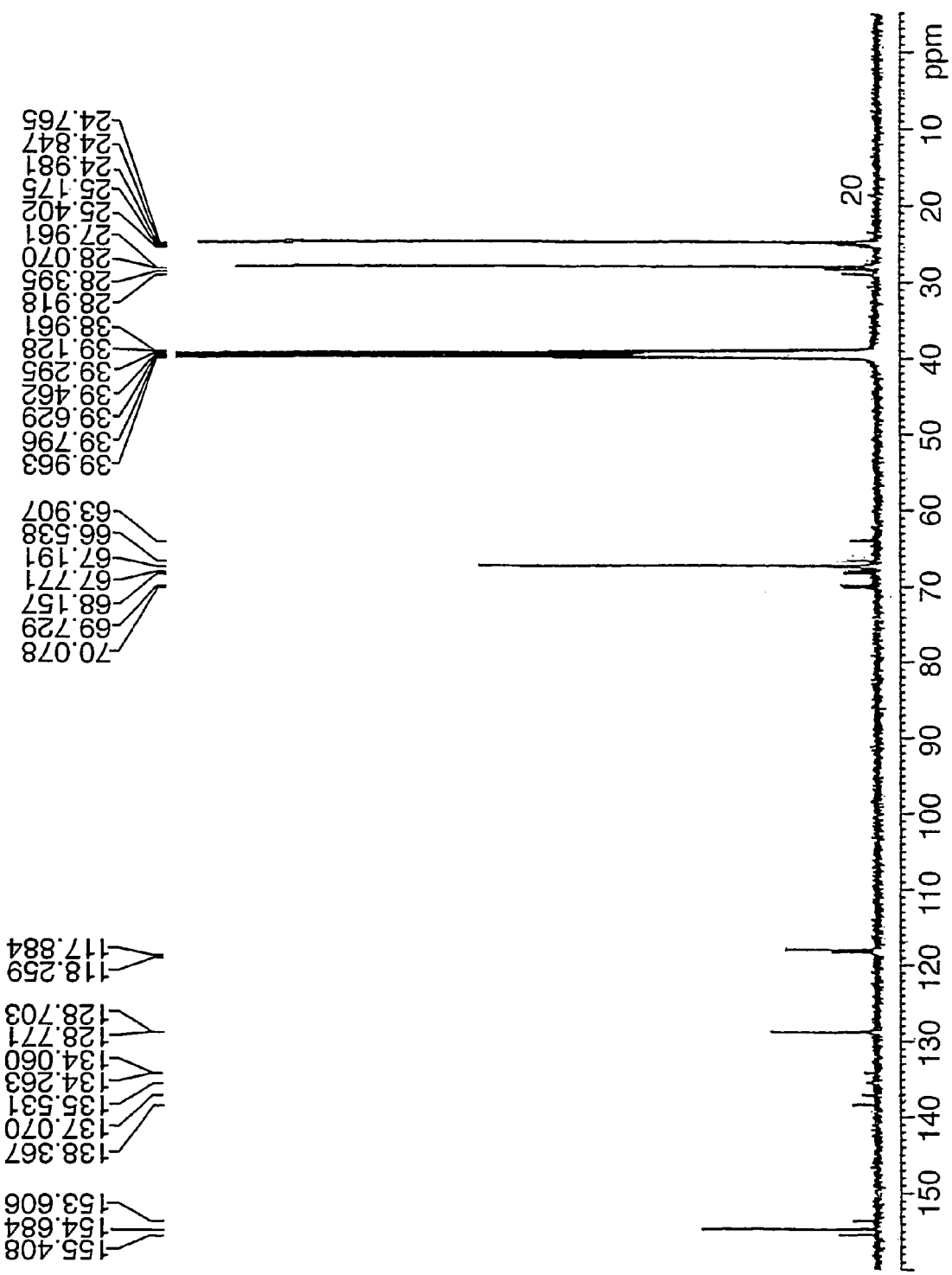
Figure 6A:
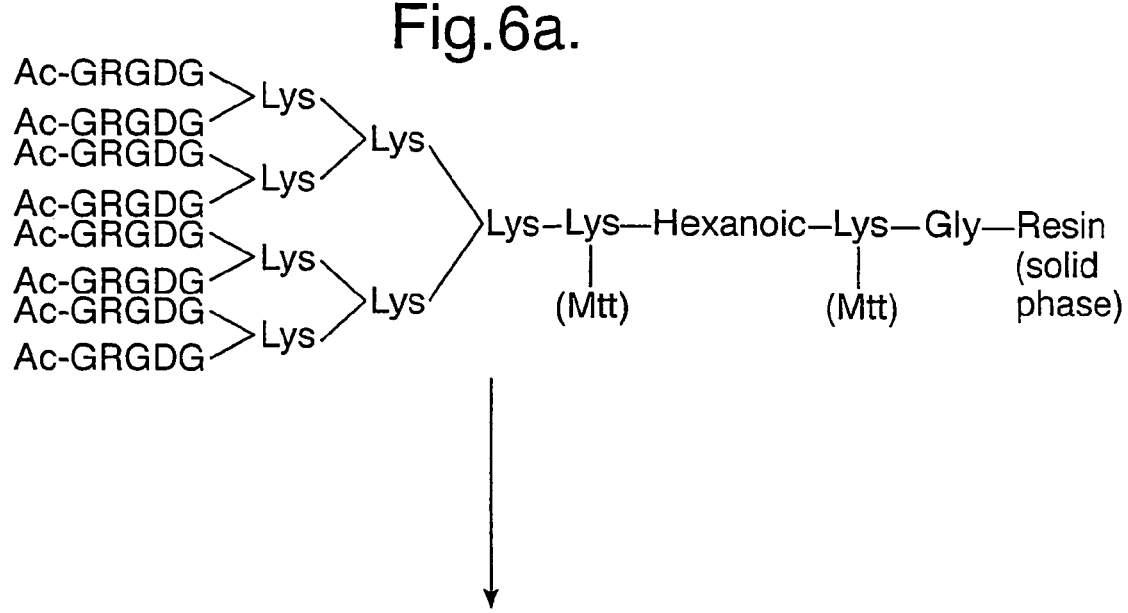
FIG. 6 depicts an example of a pendant group segment for use in the invention and schematically shows its incorporation into a polymer.
Figure 6B:
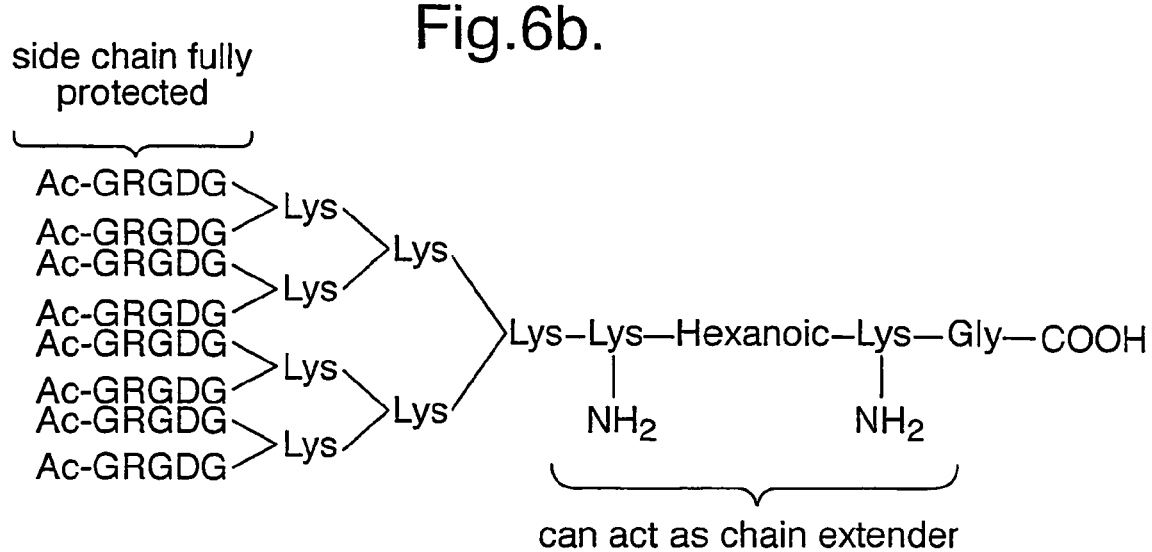
Figure 6C:
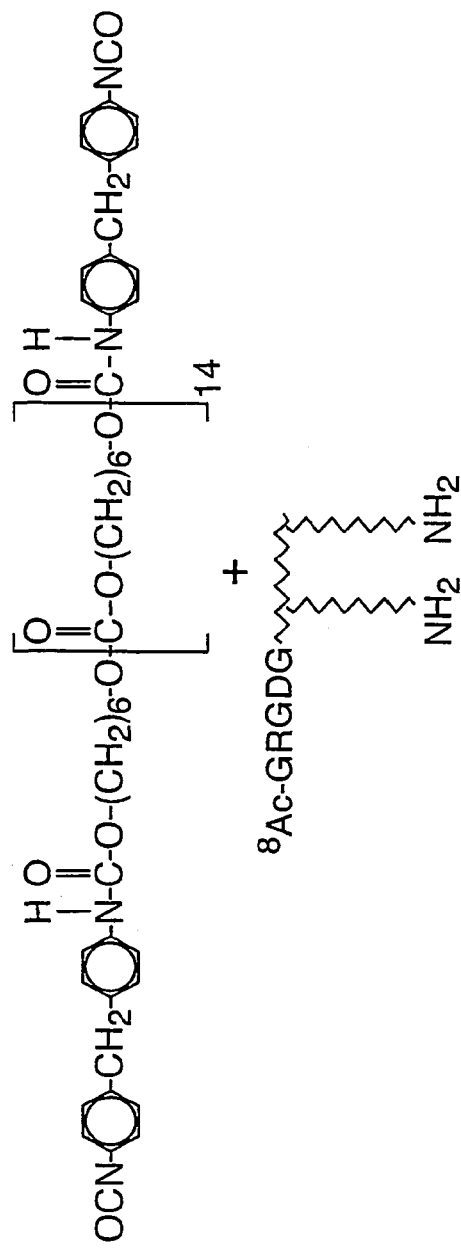
Figure 6D:
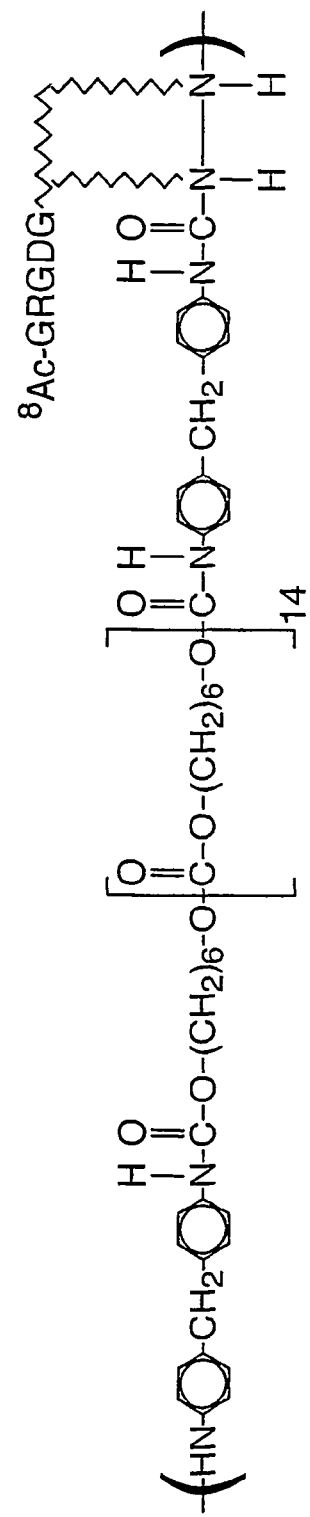

Solution state $^1$H and $^{13}$C NMR spectra were recorded on the polymer of Example 4 using a Bruker AMX500 MHz spectrometer. The polymer was dissolved in DMSO to provide samples on which measurements were made. The $^1$H and $^{13}$C NMR Spectra are depicted in FIGS. 5a and 5b respectively.

These spectra confirm that the silsesquioxane is incorporated into the polymer. The peaks for the primary and secondary hydroxyl groups in the silsesquioxane component starting material do not appear in the spectra, confirming reaction of the silsesquioxane component has occurred.

In the $^1$H NMR spectrum, the first set of peaks correspond to the aromatic groups derived from MDI and are from 7.368-7.024 ppm. The next set of peaks at 4.174-3.924 ppm correspond to the aliphatic protons. The protons of the carbonate and from the silsesquioxane appear at 4-4.2 ppm The peaks at 3.766-3.521 ppm correspond to the methylene group of the MDI-derived segment and the urethane NH. The peaks at 3.402-3.370 ppm correspond to the ethylene diamine chain extender and the protons on the pendant arm. The peaks at 0.515-0.481 and at 0.086-0.044 correspond to the $CH_3$ and $CH_2$ groups of the side chain of the silsesquioxane cage.

In the $^{13}$C NMR spectrum, the peaks at 155.408-153.606 ppm correspond to the carbonyl peaks of the urea, urethane and ester groups in that respective order. The next set of peaks are the aromatic carbons, which are from 138.367-117.884 ppm and corresponds to the carbons in the MDI. The multiple peaks at 137-139 ppm are due to conjugation, that is isomerism with the urethane group. The group of peaks at 70.-078-63.907 ppm correspond to the aliphatic carbons.

The group of peaks at 39.963-38.961 ppm correspond to the $CH_2$ of the ethylene diamine chain extender and the $CH_2$ groups of the pendant arm and of the silsesquioxane cage. The group of peaks at 28.918-18.5 ppm correspond to the polycarbonate polyol and the side chain of the silsesquioxane cage.

Example 10

Biocompatibility of Copolymer

Flat sheets of the copolymer of Example 4 were inserted into the backs of 4 sheep using standard surgical techniques. The polymers were monitored over a period of 3 months by monthly clinical examination and ultrasound scanning. No inflammation or any immunological reaction was visible.

Examples 11 to 13

Example 1 was repeated but replacing silsesquioxane 1 with Acid Yellow 29, 34 or 99 in each of Examples 11 to 13 respectively.

Example 14

72 g of dry Polycarbonate polyol (2000 mwt) and 2 g of 1,2 propanediolisobutyl-silsesquioxane (silsesquioxane 4 of FIG. 1 (POSS cage) from Sigma-Aldrich) were placed in a 500 ml reaction flask equipped with mechanical stirrer and nitrogen inlet. The mixture was heated to 130° C. to dissolve the POSS cage into the polyol and then cooled to 60° C. 18.8 g of flake MDI were added to the polyol blend and then reacted, under nitrogen, at 70° C.-80° C. for 90 minutes to form a pre-polymer. 156 g of dry dimethylacetamide were added slowly to the prepolymer to form a solution; the solution was cooled to 40° C. Chain extension of the prepolymer was carried out by drop wise addition of a mixture of 2 g of Ethylenediamine and 0.05 g of Diethylamine in 80 g of dry Dimethylacetamide. After completion of the chain extension a mixture of 4 g 1-Butanol and 80 g Dimethylacetamide were added slowly to the polymer solution.

Example 15

36 g of dry Polycarbonate polyol (2000 mwt) were placed in a 250 ml reaction flask equipped with mechanical stirrer and nitrogen inlet. 9.4 g of flake MDI were added to the polyol and reacted at 70° C.-80° C. for 90 minutes to form a pre-polymer. The pre-polymer was cooled to 50° C. and then 20 g of dry Tetrahydrofuran were added slowly to form a solution. A solution of 1 g of aminoethylaminopropylisobutyl-Silsesquioxane (Silsesquioxane 2 of FIG. 1 from Sigma-Aldrich) in 10 g of dry Tetrahydrofuran were added drop wise to the prepolymer and reacted for 40 minutes at 50° C.-60° C. 78 g of dry Dimethylacetamide were added slowly to form a solution the temperature of which was then adjusted to 40° C. Chain extension was carried out by the drop wise addition of a mixture of 1 g of Ethylenediamine and 0.025 g of Diethylamine in 40 g of dry Dimethylacetamide. After completion of the chain extension a mixture of 2 g 1-Butanol and 40 g Dimethylacetamide were added slowly to the polymer solution.

Example 16

36 g of dry Polycarbonate polyol (2000 mwt) wer placed in a 250 ml reaction flask equipped with mechanical stirrer and nitrogen inlet. 9.4 g of flake MDI were added to the polyol and reacted at 70° C.-80° C. for 90 minutes to form a pre-polymer. The pre-polymer was cooled to 50° C. and then 20 g of dry Tetrahydrofuran were added slowly to form a solution. A solution of 1 g of Diol-Silsesquioxane (Silsesquioxane 3 of FIG. 1 from Sigma-Aldrich) in 10 g of dry Tetrahydrofuran were added drop wise to the prepolymer and reacted for 60 minutes at 50° C.-60° C. 78 g of dry Dimethylacetamide were added slowly to form a solution the temperature of which was then adjusted to 40° C. Chain extension was carried out by the drop wise addition of a mixture of 1 g of Ethylenediamine and 0.025 g of Diethylamine in 40 g of dry Dimethylacetamide. After completion the chain extension a mixture of 2 g 1-Butanol and 40 g Dimethylacetmaide were added slowly to the polymer solution.

Example 17

72 g of dry Polycarbonate polyol (2000 mwt) and 2 g of trans-cyclohexanedioliso butyl-Silsesquioxane (Silsesquioxane 1 of FIG. 1 (POSS cage) from Sigma-Aldrich) were placed in a 500 ml reaction flask equipped with mechanical stirrer and nitrogen inlet. The mixture was heated to 125° C. to dissolve the POSS cage into the polyol and then cooled to 60° C. 18.8 g of flake MDI were added to the polyol blend and then reacted, under nitrogen, at 70° C.-80° C. for 90 minutes to form a pre-polymer. 156 g of dry Dimethylacetamide were added slowly to the pre-polymer to form a solution; the solution was cooled to 40° C. Chain extension of the pre-polymer was carried out by the drop wise addition of a mixture of 2 g of Ethylenediamine and 0.05 g of Diethylamine in 80 g of dry Dimethylacetamide. After completion of the chain extension a mixture of 4 g 1-Butanol and 80 g Dimethylacetamide were added slowly to the polymer solution.

Example 18

36 g of dry Polycarbonate polyol (2000 mwt) and 1 g of 1,2 propanediolisobutyl-Silsesquioxane (Silsesquioxane 4 of FIG. 1 (POSS cage) from Sigma-Aldrich) were placed in a 250 ml reaction flask equipped with mechanical stirrer and nitrogen inlet. The mixture was heated to 130° C. to dissolve the POSS cage into the polyol and then cooled to 60° C. 8.3 g of 2,4 MDI and 1.1 g of 4,4 MDI were added and then reacted, under nitrogen, at 70° C.-80° C. for 90 minutes to form a pre-polymer. 78 g dry Dimethylacetamide were added slowly to the pre-polymer to form a solution; the solution was cooled to 40° C. Chain extension of the pre-polymer was carried out by the drop wise addition of a mixture of 1 g of Ethylenediamine and 0.025 g of Diethylamine in 40 g of dry Dimethylacetamide. After completion of the chain extension a mixture of 2 g 1-Butanol and 40 g Dimethylacetamide were added slowly to the polymer solution.

Example 19

36 g of dry Polycarbonate polyol (2000 mwt) 1 g of trans-cyclohexanediolisobutyl-Silsesquioxane (Silsesquioxane 1 from FIG. 1 MOSS cage) from Sigma-Aldrich) and 0.1 g (–)-3',5'-O-(1,1,3,3-tetraisopropyl-1,3-disiloxanediyl)adenosine from Sigma-Aldrich) were placed in a 250 ml reaction flask equipped with mechanical stirrer and nitrogen inlet. The mixture was heated to 140° C. to dissolve the POSS cage and adenosine into the polyol and then cooled to 60° C. 9.5 g of flake MDI were added to the polyol blend and then reacted, under nitrogen, at 70° C.-80° C. for 90 minutes to form a pre-polymer. 78 g of dry Dimethylacetamide were added slowly to the pre-polymer to form a solution; the solution was cooled to 40° C. Chain extension of the pre-polymer was carried out by the drop wise addition of a mixture of 1 g of Ethylenediamine and 0.025 g of Diethylamine in 40 g of dry Dimethylacetamide. After completion of the chain extension a mixture of 2 g 1-Butanol and 40 g Dimethylacetamide were added slowly to the polymer solution.

Example 20

The scheme depicted in FIG. 6 shows an Example of an octameric peptide of formula (I), its protection and, schematically, its incorporation into a copolymer of the invention.

The peptide is synthesized and protected as follows:

Example 20a

Attachment of the $1^{st}$ Amino Acid Glycine Using Symmetrical Anhydride

The synthesis of a 5-residue octameric peptide Ac-Gly-Arg-Gly-$Lys^4$-$Lys^2$-Lys-Lys-Hexanoic-Lys-Gly-COOH was carried out manually by a stepwise solid phase method on a Rink-acid-resin in which 0.15 mmol of hydroxyl groups are present. The Rink resin was washed with DMF(Dimethylformamide; 10 ml/gm; 5×1 min). A solution of Fmoc-Gly (1 mmol) in DCM(Dichlromethane; 5 ml) was stirred at room temperature and activated by adding DIPCDI(Diisopropylcarbodiimide (5 eq. relative to resin loading) in dry DCM to the amino acid solution. The mixture was stirred for 15 minutes at 0° C. To this mixture 5 ml of DMF was added. The mixture was added to the resin above. DMAP (Diaminopyridine) was dissolved in DCM (0.1 eq.relative to resin loading) was added to the resin/amino acid mixture. The mixture was agitated for 1 hour with Oxygen free Nitrogen gas.

Example 20b

Sequential Addition of Protected Amino Acids

The Rink-Glycine resin was placed in a sintered glass vessel and acylated with active esters formed in-situ from pre-weighted protected Fmoc amino acids or Fmoc Aminohexonoic acid in the presence of the activating agent HBTU the base-initiated carboxyl activation was performed by adding 1 equivalent of HBTU [2-(1H-Benzotriazole-1-yl)-1,1,3, 3-tetramethyluronium hexafluorophosphate), 1 equivalent of HOBT solution in DMF containing 2 equivalents of DIPEA. A 5 fold excess (based on the resin loading) of acylating species with the following equivalents: amino acid: HBTU: MMP (1:1:2) in DMF were used in all subsequent coupling. The cycle for the addition of activated amino acid consisted of a 10×1 min wash of the solid support, with 20% piperidine in DMF (2×5 min) to cleave the $N^\alpha$-Fmoc group, 10×1 min DMF wash, 30 min aclation reaction with 5 equivalents of an Fmoc-amino acid HBTU ester, and 10×1 min DMF wash for a total cycle time of about 60 minutes.

Example 20c

Assembly of the Octameric Ac-Gly-Arg-Asp-Gly-Lys4-Lys2-Lys-Lys-Ahx-Lys-Gly-Rink-acid-rasin The synthesis of the 5-residue octameric peptide was accomplished manually in a stepwise solid-phase procedure on the preloaded Fmoc-Lys-Ahx-Lys-Gly-resin. The resin was put through normal deprotection cycle with 20% piperidine in DMF to remove the Fmoc on the monovalent Lysine. The synthesis of the $1^{st}$, $2^{nd}$ and $3^{rd}$ level of the Lysine template was achieved using 5 molar excess (based on the resin loading) of activated active ester of the $N^\alpha$,$N^\epsilon$-Fmoc-Lysine (Fmoc) in DMF. The resin was finally deprotected with 20% piperidine in DMF for (2×5 min) to expose the 8 functional amino groups. The resin was washed with DMF (10×1 min). A 5-fold excess (based on the new loading) of acylating species in 0.2 MMP in DMF were added in all subsequent coupling as described above leading to the completion of the GRGD sequence onto the Octavalent Lysines. The completed peptides was acetylated with acetic anhydride in DMF in order to protect the amino terminus. The octameric protected peptide was released from the solid phase with dilute trifloroacetic acid (TFA) in DCM with the two $N^\epsilon$ of Lysines at the carboxyl terminus deprotected simultaneously. The product was checked by HPLC for purity and used in the polymerization of the main poly(carbonate urethane).

Example 20d

Production of Polymer 36 g of dry Polycarbonate polyol (2000 mwt) 1 g of trans-cyclohexanediolisobutyl-Silsesquioxane (Silsesquioxane 4 of FIG. 1 (POSS cage) from Sigma-Aldrich) were placed in a 250 ml reaction flask equipped with mechanical stirrer and nitrogen inlet. The mixture was heated to 125° C. to dissolve the POSS cage into the polyol and then cooled to 60° C. 9.56 g of flake MDI were added to the polyol blend and reacted, under nitrogen, at 70° C.-80° C. for 90 minutes to form a pre-polymer. 20 g of dry Dimethylacetamide were added slowly to the pre-polymer to form a solution; the solution was cooled to 55° C. 103 mgm of the octomer produced as described above dissolved in 10 g dry dimethylacetamide wer added and reacted in at 50° C.-60° C. for 45 minutes. A further 48 g of dry Dimethylacetamide wer added slowly and the temperature adjusted to 40° C. Chain extension of the pre-polymer was carried out by the drop wise addition of a mixture of 1 g of Ethylenediamine and 0.025 g of Diethylamine in 40 g of dry Dimethylacetamide. After completion of the chain extension a mixture of 2 g 1-Butanol and 40 g Dimethylacetamide were added slowly to the polymer solution

The invention claimed is:

1. A copolymer comprising (a) one or more pendant group segments and (b) one or more polyol segments, each of said segments being linked to one or more further segments which may be the same or different,
   wherein said one or more pendant group segments are the same or different and are siloxane segments, wherein each of said siloxane segments comprises a siloxane moiety which is either a linear siloxane with a molecular weight of up to 2000 Daltons, a silsesquioxane cage or a partial silsesquioxane cage, said moiety being attached to the copolymer backbone either directly or via a pendant arm that does not contain any ether groups, and wherein when said moiety is a silsesquioxane cage or partial silsesquioxane cage, then the molar ratio of pendant group segments to polyol segments is 1:X wherein X is 10 or more, and wherein when said moiety is a linear siloxane, then the component (b) comprises one or more polycarbonate segments.

2. A copolymer according to claim 1, wherein the segments are linked via urea or urethane linkages.

3. A process for producing a copolymer according to claim 2, wherein said process comprises polymerising, in any order,
   (i) one or more pendant group siloxane segments, wherein each of said siloxane segments comprises a siloxane moiety which is either a linear siloxane with a molecular weight of up to 2000 Daltons, a silsesquioxane cage or a partial silsesquioxane cage, said moiety being attached to the copolymer backbone either directly or via a pendant arm that does not contain any ether groups, and wherein when said moiety is a silsesquioxane cage or partial silsesquioxane cage, then the molar ratio of pendant group segments to polyol segments is 1:X wherein X is 10 or more, and wherein each of said one or more segments is bonded to at least one group selected from primary or secondary amine, hydroxyl and carboxylic acid groups;
   (ii) a polyol;
   (iii) an aromatic compound having two or more isocyanate groups; and optionally
   (iv) one or more chain extenders selected from amino acids, peptides, polypeptides and $C_1$-$C_6$ aliphatic groups, each of which has at least one substituent selected from primary or secondary amine, hydroxyl and carboxylic acid groups,
   wherein if the siloxane moiety in (i) is a linear siloxane, then the polyol (ii) comprises one or more polycarbonate segments.

4. A copolymer obtained by the process of claim 3.

5. A process for producing a copolymer according to claim 2, said copolymer comprising a linear siloxane attached directly to the backbone of the copolymer,
   wherein said process comprises (i) reacting a polyol polyurethane with a strong base, and (ii) reacting the product of (i) with a siloxane.

6. A copolymer according to claim 1, wherein the pendant siloxane segment(s) comprise a linear siloxane moiety, said linear siloxane moiety comprising repeating units of the formula (II)

wherein each R is the same or different and represents an aliphatic or aromatic group.

7. A copolymer according to claim 6, wherein each R is the same or different and represents an alkyl, alkenyl, alkynyl, cycloalkyl or aryl group.

8. A copolymer according to claim 1 wherein the molar ratio of siloxane segment(s) to polyol segment(s) is 1:10 or less.

9. A copolymer according to claim 8 wherein the ratio of pendant siloxane segment:polyol segment is 1:25 or less.

10. A copolymer according to claim 1, which comprises one or more pendant siloxane segments having a molecular weight of up to 5000.

11. A copolymer according to claim 1, which comprises two or more different pendant siloxane segments, each containing a silsesquioxane cage or partial cage.

12. A copolymer according to claim 1 which comprises two or more different pendant group segments.

13. A copolymer according to claim 1, further comprising (c) one or more chain extender segments, each of said chain extender segments being linked to one or more further segments, which may be the same or different.

14. A copolymer according to claim 13, wherein said chain extender segment(s) are selected from amino acids, peptides, polypeptides and $C_1$-$C_6$ aliphatic moieties.

15. A copolymer according to claim 14, wherein one or more of said chain extender segment(s) is an anticoagulant.

16. A copolymer according to claim 14, wherein one or more of said chain extender segment(s) is RGD (Arg-Gly-Asp).

17. A copolymer according to claim 1, which comprises as component (b) one or more polycarbonate segment(s).

18. A process for producing a lined copolymer, wherein said process comprises seeding cells onto the surface of a copolymer as claimed in claim 1.

19. A lined copolymer obtained by the process of claim 18.

20. A moulded article comprising a copolymer as claimed in claim 1 or a lined copolymer as claimed in claim 19.

21. A moulded article according to claim 20 which is an implantable device.

22. An implantable device according to claim 21 which is a vascular graft.

23. A method of treating a human or animal patient in need of the replacement of a body part, said method comprising replacing said body part with the implantable device of claim 21.

24. A copolymer according to claim 1 wherein the siloxane group is attached to the polymer via a pendant arm.

25. A copolymer according to claim 24, wherein the pendant siloxane segment(s) have the structure (III)

 (III)

wherein S is a linear siloxane group, a silsesquioxane cage or a partial silsesquioxane cage and Y is an aliphatic group which is bonded to at least two urea or urethane linkages.

26. A copolymer according to claim 25, wherein S is a silsesquioxane cage.

27. A copolymer according to claim 26, wherein the silsesquioxane cage S consists of repeating units of formula (IV)

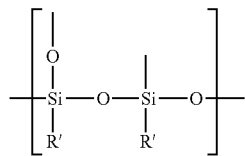 (IV)

wherein each R' is the same or different and represents an aliphatic or aromatic group and wherein one R' group is replaced with a bond attached to group Y.

28. A copolymer according to claim 27, wherein each R' is the same or different and represents an alkyl, alkenyl, alkynyl, cycloalkyl or aryl group.

29. A copolymer according to claim 24 wherein the pendant arm is attached at the end of the copolymer chain.

30. A copolymer according to claim 1, wherein each segment is linked to one or more further segments by a group of formula

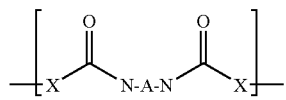

wherein each X is the same or different and is a nitrogen or oxygen atom and each A is the same or different and is an aromatic or aliphatic moiety.

31. A copolymer according to claim 1, which comprises one or more further pendant group segments which may be the same or different and are selected from:

(1) segments containing phosphoryl choline or a derivative thereof or segments(s) of formula (VII)

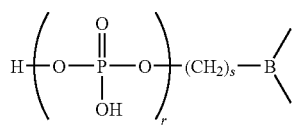

wherein s is 0, 1, 2, 3 or 4 and B is an aliphatic group of formula

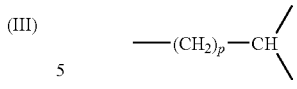

wherein p is an integer of from 0 to 8, or B is a group of formula (VI) or (VIA)

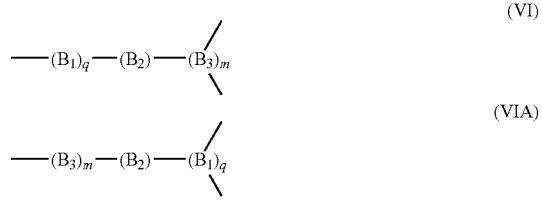 (VI)

(VIA)

wherein each $B_1$ is the same or different and is a $C_6$-$C_{10}$ arylene, a $C_1$-$C_8$ alkylene, $C_2$-$C_8$ alkenylene, $C_3$-$C_6$ cycloalkylene group or a 5- or 6-membered heterocyclyl group containing 1, 2 or 3 heteroatoms selected from nitrogen, oxygen and sulfur; $B_2$ is a 5- to 10-membered heterocyclyl or heteroaryl group containing from 1 to 5 heteroatoms selected from nitrogen, oxygen and sulfur; $B_3$ is an aliphatic group; q is 0, 1, 2 or 3; and m is 0 or 1, and r is 1, 2, 3, 4 or 5, and wherein the one or more of the —OH groups on the phosphate groups are, independently optionally present in the form of a salt;

(2) segments containing a di- or trifluoromethyl group;
(3) heparin-like segments containing a group of formula (XII)

wherein D is an aliphatic or aromatic group and Ar—$SO_3^-$ comprises one or more linked aryl and/or heteroaryl groups, at least one of the aryl and/or heteroaryl groups having an $SO_3^-$ substituent; and (4) segments containing a group of formula (I)

$[P]_{n'}$-$[Lys]_n$-Lys-[Spacer]-Lys-$[Al]_x$   (I)

wherein:
[Al] is an inert amino acid;
x is 0, 1, 2 or 3;
[Spacer] is a fatty acid, amino acid, peptide or PEG;
$[P]_{n'}$-$[Lys]_n$ is a dendritic structure formed from n lysine groups and n' groups P;
n is an integer of from 1 to 15;
n' is zero or an integer of up to 16; and
each P is the same or different and is an amino acid or a peptide having up to 25 amino acids, and wherein at least a part of each of said pendant group segment(s) is on a side chain of the copolymer.

32. A copolymer according to claim 31, wherein the segment(s) containing phosphoryl choline or a derivative thereof have the formula (V)

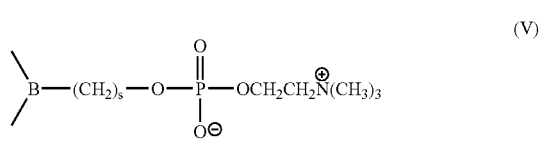 (V)

wherein s is 0, 1, 2, 3 or 4 and B is an aliphatic group of formula

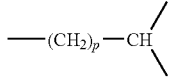

wherein p is an integer of from 0 to 8, or B is a group of formula (VI) or (VIA)

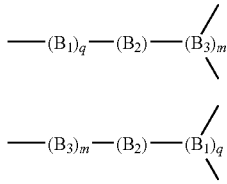

(VI)

(VIA)

wherein each $B_1$ is the same or different and is a $C_6$-$C_{10}$ arylene, a $C_1$-$C_8$ alkylene, $C_2$-$C_8$ alkenylene, $C_3$-$C_6$ cycloalkylene group or a 5- or 6-membered heterocyclyl group containing 1, 2 or 3 heteroatoms selected from nitrogen, oxygen and sulfur; $B_2$ is a 5- to 10-membered heterocyclyl or heteroaryl group containing from 1 to 5 heteroatoms selected from nitrogen, oxygen and sulfur; $B_3$ is an aliphatic group; q is 0, 1, 2 or 3; and m is 0 or 1.

33. A copolymer according to claim 31, wherein the segment(s) containing a di- or trifluoromethyl group are straight or branched, $C_{2-12}$ alkylene groups which are substituted with one or more di- or trifluoromethyl groups and optionally one or more fluorine atoms.

34. A copolymer according to claim 31, wherein the segments(s) containing a di- or trifluoromethyl group are siloxane segments, segments containing phosphoryl choline or a derivative or analogue thereof, heparin-like segments or segments of formula (I) which are substituted with a di- or trifluoromethyl group, wherein said segments containing an analogue of phosphoryl choline are segments of formula (VII)

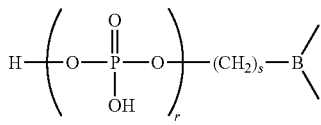

(VII)

wherein s is 0, 1, 2, 3 or 4 and B is an aliphatic group of formula

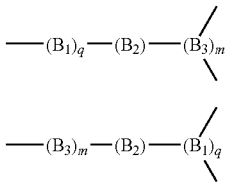

wherein p is an integer of from 0 to 8, or B is a group of formula (VI) or (VIA)

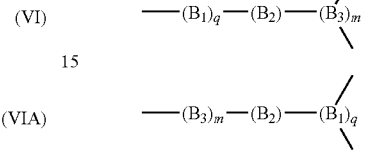

(VI)

(VIA)

wherein each $B_1$ is the same or different and is a $C_6$-$C_{10}$ aryl, a $C_1$-$C_8$ alkylene, $C_2$-$C_8$ alkenylene, $C_3$-$C_6$ cycloalkyl group or a 5- or 6- membered heterocyclyl group containing 1, 2 or 3 heteroatoms selected from nitrogen, oxygen and sulfur; $B_2$ is a 5- to 10-membered heterocyclyl or heteroaryl group containing from 1 to 5 heteroatoms selected from nitrogen, oxygen and sulfur; $B_3$ is an aliphatic group; q is 0, 1, 2 or 3; and m is 0 or 1, and r is 1, 2, 3, 4 or 5, and wherein the one or more of the —OH groups on the phosphate groups are, independently optionally present in the form of a salt.

35. A copolymer according to claim 31, wherein in the group of formula (XII) Ar comprises one or two linked aryl or heteroaryl groups selected from phenylene and pyrazolylene, Ar being substituted with one or two —$SO_3^-$ groups and one, two or three further substituents selected from methyl, ethyl, methoxy, methylthio, nitro and dimethylamino groups; and D is a group $D^1$-$D^2$-$D^3$- wherein $D^1$ is an arylene or heteroarylene group which is unsubstituted or substituted with one, two or three substituents selected from methyl, ethyl and methoxy groups, $D^2$ is —NR'CO—, —CONR', —OCO—, —COO—, —NR'SO$_2$— or —SO$_2$NR'— wherein each R' is the same or different and is hydrogen or a $C_{1-4}$ alkyl group and $D^3$ is phenylene or a $C_{1-4}$ alkylene or $C_{2-4}$ alkenylene group which is unsubstituted or substituted with one, two or three substituents selected from methyl, ethyl and methoxy groups.

36. A copolymer according to claim 31, wherein the group of formula (XII) is a derivative of an Acid Yellow compound.

37. A copolymer according to claim 31, wherein in the group of formula (I), n is 7.

38. A copolymer according to claim 31, wherein in the group of formula (I), P is an amino acid or peptide in the D-form.

* * * * *